(12) United States Patent
Dai et al.

(10) Patent No.: US 10,593,941 B2
(45) Date of Patent: Mar. 17, 2020

(54) CATHODE ACTIVE MATERIALS HAVING IMPROVED PARTICLE MORPHOLOGIES

(71) Applicant: Apple Inc., Cupertino, CA (US)

(72) Inventors: Hongli Dai, Los Altos, CA (US);
Huiming Wu, San Jose, CA (US);
Dapeng Wang, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 99 days.

(21) Appl. No.: 16/057,388

(22) Filed: Aug. 7, 2018

(65) Prior Publication Data

US 2018/0351173 A1 Dec. 6, 2018

Related U.S. Application Data

(60) Division of application No. 15/804,106, filed on Nov. 6, 2017, now Pat. No. 10,084,187, which is a
(Continued)

(51) Int. Cl.
*H01M 4/505* (2010.01)
*C01G 51/00* (2006.01)
(Continued)

(52) U.S. Cl.
CPC ............ *H01M 4/505* (2013.01); *C01G 51/00* (2013.01); *C01G 51/04* (2013.01); *C01G 51/50* (2013.01);
(Continued)

(58) Field of Classification Search
CPC ............ H01M 4/505; H01M 10/0525; H01M 4/1391; H01M 2/1016; H01M 4/525;
(Continued)

(56) References Cited

U.S. PATENT DOCUMENTS 5,744,262 A 4/1998 Cheng et al.
6,007,947 A 12/1999 Mayer
(Continued)

FOREIGN PATENT DOCUMENTS

CN 1588675 3/2005
CN 1702891 11/2005
(Continued)

OTHER PUBLICATIONS

U.S. Appl. No. 16/004,941, filed Jun. 6, 2018, Dai et al.
(Continued)

*Primary Examiner* — Stewart A Fraser
(74) *Attorney, Agent, or Firm* — Polsinelli PC

(57) ABSTRACT

Mixed-metal oxides and lithiated mixed-metal oxides are disclosed that involve compounds according to, respectively, $Ni_xMn_yCo_zMe_\alpha O_\beta$ and $Li_{1+\gamma}Ni_xMn_yCo_zMe_\alpha O_\beta$. In these compounds, Me is selected from B, Na, Mg, Al, Si, K, Ca, Sc, Ti, V, Cr, Fe, Cu, Zn, Ga, Ge, Zr, Nb, Mo, Ru, Ag, In, and combinations thereof; $0 \leq x \leq 1$; $0 \leq y \leq 1$; $0 \leq z < 1$; $x+y+z>0$; $0 \leq \alpha \leq 0.5$; and $x+y+\alpha>0$. For the mixed-metal oxides, $1 \leq \beta \leq 5$. For the lithiated mixed-metal oxides, $-0.1 \leq \gamma \leq 1.0$ and $1.9 \leq \beta \leq 3$. The mixed-metal oxides and the lithiated mixed-metal oxides include particles having an average density greater than or equal to 90% of an ideal crystalline density.

11 Claims, 13 Drawing Sheets

Related U.S. Application Data continuation of application No. 15/709,961, filed on Sep. 20, 2017, now Pat. No. 10,297,823.

(60) Provisional application No. 62/397,019, filed on Sep. 20, 2016.

(51) Int. Cl.

| | | |
|---|---|---|
| *C01G 51/04* | (2006.01) | |
| *C01G 53/00* | (2006.01) | |
| *H01M 4/131* | (2010.01) | |
| *H01M 4/485* | (2010.01) | |
| *H01M 4/525* | (2010.01) | |
| *H01M 2/10* | (2006.01) | |
| *H01M 4/1391* | (2010.01) | |
| *H01M 10/0525* | (2010.01) | |
| *C01D 15/02* | (2006.01) | |
| *C01G 45/00* | (2006.01) | |
| *G01N 23/20* | (2018.01) | |

(52) U.S. Cl.
CPC ............ *C01G 51/66* (2013.01); *C01G 53/50* (2013.01); *H01M 2/1016* (2013.01); *H01M 4/131* (2013.01); *H01M 4/1391* (2013.01); *H01M 4/485* (2013.01); *H01M 4/525* (2013.01); *H01M 10/0525* (2013.01); *C01D 15/02* (2013.01); *C01G 45/006* (2013.01); *C01G 51/006* (2013.01); *C01G 53/006* (2013.01); *C01P 2002/72* (2013.01); *C01P 2002/76* (2013.01); *C01P 2002/77* (2013.01); *C01P 2004/03* (2013.01); *C01P 2004/51* (2013.01); *C01P 2004/61* (2013.01); *C01P 2006/10* (2013.01); *C01P 2006/11* (2013.01); *G01N 23/20075* (2013.01)

(58) Field of Classification Search
CPC ...... H01M 4/485; H01M 4/131; C01G 53/50; C01G 51/66; C01G 51/50
See application file for complete search history.

(56) References Cited

U.S. PATENT DOCUMENTS

| | | | |
|---|---|---|---|
| 6,077,496 A | 6/2000 | Hiraoka et al. | |
| 6,677,082 B2 | 1/2004 | Thackeray et al. | |
| 6,680,143 B2 | 1/2004 | Thackeray et al. | |
| 6,878,487 B2 | 4/2005 | Cho et al. | |
| 7,135,252 B2 | 11/2006 | Thackeray et al. | |
| 7,205,072 B2 | 4/2007 | Kang et al. | |
| 7,238,450 B2 | 6/2007 | Howard, Jr. et al. | |
| 7,314,682 B2 | 1/2008 | Thackeray et al. | |
| 7,314,684 B2 | 1/2008 | Kang et al. | |
| 7,435,402 B2 | 10/2008 | Kang et al. | |
| 7,468,223 B2 | 12/2008 | Thackeray et al. | |
| 7,655,361 B2 | 2/2010 | Kim et al. | |
| 7,732,096 B2 | 6/2010 | Thackeray et al. | |
| 7,754,384 B2 | 7/2010 | Patoux et al. | |
| 7,897,674 B2 | 3/2011 | Zaghib | |
| 7,923,149 B2 | 4/2011 | Hwang et al. | |
| 8,148,011 B2 | 1/2012 | Thackeray et al. | |
| 8,187,746 B2 | 5/2012 | Chen et al. | |
| 8,206,852 B2 | 6/2012 | Chang et al. | |
| 8,277,683 B2 | 10/2012 | Deng et al. | |
| 8,337,727 B2 | 12/2012 | Chen et al. | |
| 8,383,077 B2 | 2/2013 | Thackeray et al. | |
| 8,801,960 B2 | 8/2014 | Ueda et al. | |
| 8,802,290 B2 | 8/2014 | Li et al. | |
| 9,166,222 B2 | 10/2015 | Amiruddin et al. | |
| 9,716,265 B2 | 7/2017 | Dai et al. | |
| 10,084,187 B2 * | 9/2018 | Dai ........................ | C01G 53/50 |
| 10,128,494 B2 | 11/2018 | Dai et al. | |
| 10,141,572 B2 | 11/2018 | Wu et al. | |
| 10,164,256 B2 | 12/2018 | Wu et al. | |
| 10,297,821 B2 | 5/2019 | Dai et al. | |
| 10,297,823 B2 * | 5/2019 | Dai ........................ | H01M 4/505 |
| 2002/0061444 A1 | 5/2002 | Kweon et al. | |
| 2002/0114995 A1 | 8/2002 | Thackeray | |
| 2002/0136954 A1 | 9/2002 | Thackeray | |
| 2002/0182504 A1 | 12/2002 | Imachi et al. | |
| 2003/0039886 A1 | 2/2003 | Zhang et al. | |
| 2003/0073002 A1 | 4/2003 | Imachi et al. | |
| 2003/0082445 A1 | 5/2003 | Smieth et al. | |
| 2003/0134200 A1 | 7/2003 | Tanaka et al. | |
| 2004/0029008 A1 | 2/2004 | Winterberg | |
| 2004/0191633 A1 | 9/2004 | Johnson et al. | |
| 2004/0258836 A1 | 12/2004 | Besenhard et al. | |
| 2005/0026040 A1 | 3/2005 | Thackery | |
| 2005/0074675 A1 | 4/2005 | Nishijima et al. | |
| 2005/0130042 A1 | 6/2005 | Liu et al. | |
| 2005/0136329 A1 | 6/2005 | Howard, Jr. et al. | |
| 2005/0265909 A1 | 12/2005 | Kajiya et al. | |
| 2005/0271948 A1 | 12/2005 | Kang | |
| 2006/0024584 A1 | 2/2006 | Kim et al. | |
| 2006/0068293 A1 | 3/2006 | Kim et al. | |
| 2006/0081818 A1 | 4/2006 | Ito et al. | |
| 2006/0088767 A1 | 4/2006 | Li et al. | |
| 2006/0099508 A1 | 5/2006 | Thackeray et al. | |
| 2006/0159994 A1 | 7/2006 | Dahn et al. | |
| 2006/0177739 A1 | 8/2006 | Endo et al. | |
| 2006/0194118 A1 | 8/2006 | Yew et al. | |
| 2006/0240326 A1 | 10/2006 | Lee | |
| 2007/0141469 A1 | 6/2007 | Tokunaga et al. | |
| 2007/0172739 A1 | 7/2007 | Visco | |
| 2007/0202407 A1 | 8/2007 | Eberman et al. | |
| 2008/0057401 A1 | 3/2008 | Mori et al. | |
| 2008/0090150 A1 | 4/2008 | Nakura | |
| 2008/0118836 A1 | 5/2008 | Hwang et al. | |
| 2008/0118847 A1 | 5/2008 | Jung et al. | |
| 2008/0131778 A1 | 6/2008 | Watanabe et al. | |
| 2008/0160415 A1 | 7/2008 | Wakita et al. | |
| 2008/0280205 A1 | 11/2008 | Jiang et al. | |
| 2008/0311473 A1 | 12/2008 | Sasaoka et al. | |
| 2008/0318131 A1 | 12/2008 | Watanabe et al. | |
| 2009/0092903 A1 | 4/2009 | Johnson et al. | |
| 2009/0146115 A1 | 6/2009 | Xiao et al. | |
| 2009/0200510 A1 | 8/2009 | Watanabe et al. | |
| 2009/0202905 A1 | 8/2009 | Morita et al. | |
| 2009/0239148 A1 | 9/2009 | Jiang | |
| 2010/0055567 A1 | 4/2010 | Nakai et al. | |
| 2010/0086853 A1 | 4/2010 | Venkatachalam et al. | |
| 2010/0086854 A1 | 4/2010 | Kumar et al. | |
| 2010/0151332 A1 | 6/2010 | Lopez et al. | |
| 2010/0173197 A1 | 7/2010 | Li et al. | |
| 2010/0304225 A1 | 12/2010 | Pascaly et al. | |
| 2011/0014518 A1 | 1/2011 | Nakai et al. | |
| 2011/0017529 A1 | 1/2011 | Kumar et al. | |
| 2011/0031437 A1 | 2/2011 | Nagase et al. | |
| 2011/0052981 A1 | 3/2011 | Lopez et al. | |
| 2011/0053001 A1 | 3/2011 | Babic et al. | |
| 2011/0076556 A1 | 3/2011 | Karthikeyan et al. | |
| 2011/0076564 A1 | 3/2011 | Yu et al. | |
| 2011/0089369 A1 | 4/2011 | Patoux et al. | |
| 2011/0111294 A1 | 5/2011 | Lopez et al. | |
| 2011/0111298 A1 | 5/2011 | Lopez et al. | |
| 2011/0121240 A1 | 5/2011 | Amine et al. | |
| 2011/0136019 A1 | 6/2011 | Amiruddin et al. | |
| 2011/0143174 A1 | 6/2011 | Kim | |
| 2011/0165474 A1 | 7/2011 | Im et al. | |
| 2011/0171371 A1 | 7/2011 | Li et al. | |
| 2011/0171539 A1 | 7/2011 | Patoux et al. | |
| 2011/0200864 A1 | 8/2011 | Dai | |
| 2011/0200880 A1 | 8/2011 | Yu | |
| 2011/0223492 A1 | 9/2011 | Sakitani et al. | |
| 2011/0244331 A1 | 10/2011 | Karthikeyan et al. | |
| 2011/0294006 A1 | 12/2011 | Amine et al. | |
| 2011/0294019 A1 | 12/2011 | Amine et al. | |
| 2012/0040247 A1 | 2/2012 | Manivannan et al. | |
| 2012/0168696 A1 | 5/2012 | Huang et al. | |
| 2012/0196176 A1 | 8/2012 | He et al. | |
| 2012/0282522 A1 | 11/2012 | Axelbaum et al. | |
| 2012/0295155 A1 | 11/2012 | Deng et al. | |

(56) References Cited

U.S. PATENT DOCUMENTS

| | | |
|---|---|---|
| 2013/0004826 A1 | 1/2013 | Li et al. |
| 2013/0011738 A1 | 1/2013 | Zhou |
| 2013/0101893 A1 | 4/2013 | Dai et al. |
| 2013/0149604 A1 | 6/2013 | Fujiki et al. |
| 2013/0252107 A1 | 9/2013 | Lee et al. |
| 2014/0087065 A1 | 3/2014 | Li et al. |
| 2014/0087254 A1 | 3/2014 | Li et al. |
| 2014/0087256 A1 | 3/2014 | Li et al. |
| 2014/0087261 A1 | 3/2014 | Li et al. |
| 2014/0141331 A1 | 5/2014 | Lee et al. |
| 2014/0158932 A1 | 6/2014 | Sun et al. |
| 2014/0175329 A1 | 6/2014 | Palma et al. |
| 2014/0234715 A1 | 8/2014 | Fasching et al. |
| 2014/0272563 A1 | 9/2014 | Dai et al. |
| 2015/0140421 A1 | 5/2015 | Ihara et al. |
| 2015/0171423 A1 | 6/2015 | Kim et al. |
| 2015/0243971 A1 | 8/2015 | Cho et al. |
| 2015/0243984 A1 | 8/2015 | Kase et al. |
| 2015/0303519 A1 | 10/2015 | Hanazaki |
| 2015/0311522 A1 | 10/2015 | Fang et al. |
| 2016/0036043 A1 | 2/2016 | Dai et al. |
| 2016/0156032 A1 | 6/2016 | Lee et al. |
| 2016/0293941 A1 | 10/2016 | Yamasaki et al. |
| 2016/0315315 A1 | 10/2016 | Olken et al. |
| 2017/0092949 A1 | 3/2017 | Dai et al. |
| 2017/0133678 A1 | 5/2017 | Ozoemena et al. |
| 2017/0214045 A1 | 7/2017 | Dai et al. |
| 2017/0263917 A1 | 9/2017 | Dai et al. |
| 2017/0263928 A1 | 9/2017 | Dai et al. |
| 2017/0263929 A1 | 9/2017 | Wu et al. |
| 2017/0346082 A1 | 11/2017 | Dai et al. |
| 2018/0062156 A1 | 3/2018 | Wu et al. |
| 2018/0079655 A1 | 3/2018 | Dai et al. |
| 2018/0083277 A1 | 3/2018 | Dai et al. |
| 2018/0083278 A1 | 3/2018 | Dai et al. |
| 2018/0114983 A9 | 4/2018 | Dai et al. |
| 2018/0114984 A9 | 4/2018 | Wu et al. |
| 2018/0123117 A9 | 5/2018 | Dai et al. |
| 2018/0215629 A1 | 8/2018 | Honma et al. |
| 2018/0257947 A9 | 9/2018 | Dai et al. |
| 2018/0294522 A1 | 10/2018 | Dai et al. |
| 2019/0027747 A9 | 1/2019 | Dai et al. |
| 2019/0067686 A1 | 2/2019 | Dai et al. |
| 2019/0074514 A1 | 3/2019 | Wu et al. |

FOREIGN PATENT DOCUMENTS

| | | |
|---|---|---|
| CN | 1770514 | 10/2006 |
| CN | 101150190 | 3/2008 |
| CN | 101223660 | 7/2008 |
| CN | 101284681 | 10/2008 |
| CN | 101510603 | 8/2009 |
| CN | 101694877 | 4/2010 |
| CN | 101734728 | 6/2010 |
| CN | 102110808 | 6/2011 |
| CN | 102299299 | 12/2011 |
| CN | 102332585 | 1/2012 |
| CN | 102368548 | 3/2012 |
| CN | 101789499 | 4/2012 |
| CN | 102479947 | 5/2012 |
| CN | 102484249 | 5/2012 |
| CN | 102544575 | 7/2012 |
| CN | 102646831 | 8/2012 |
| CN | 102683666 | 9/2012 |
| CN | 102723459 | 10/2012 |
| CN | 102751481 | 10/2012 |
| CN | 102881891 | 1/2013 |
| CN | 103151520 | 6/2013 |
| CN | 103296249 | 9/2013 |
| CN | 102386381 | 1/2014 |
| CN | 103560250 | 2/2014 |
| CN | 103872302 | 6/2014 |
| CN | 103872315 | 6/2014 |
| CN | 103972493 | 8/2014 |
| CN | 104022280 | 9/2014 |
| CN | 104466099 | 3/2015 |
| CN | 104868122 | 8/2015 |
| CN | 106450211 | 2/2017 |
| DE | 10352063 | 6/2005 |
| JP | 4-267053 | 9/1992 |
| JP | H-10-087327 | 4/1998 |
| JP | 2005-101003 | 4/2005 |
| JP | 2005-289700 | 10/2005 |
| JP | 2009-4311 | 1/2009 |
| JP | 2015-213038 | 11/2015 |
| KR | 10-2002-0063501 | 8/2002 |
| KR | 10-2014-0073856 | 6/2014 |
| KR | 101731473 | 4/2017 |
| TW | 201126798 | 8/2011 |
| TW | 201342695 | 10/2013 |
| WO | WO 2004/045015 | 5/2004 |
| WO | WO 2004/107480 | 12/2004 |
| WO | WO 2008/069351 | 6/2008 |
| WO | WO 2009/120515 | 10/2009 |
| WO | WO 2010/011569 | 1/2010 |
| WO | WO 2010/139404 | 12/2010 |
| WO | WO 2011/020073 | 2/2011 |
| WO | WO 2011/054441 | 5/2011 |
| WO | WO 2013/048048 | 4/2013 |
| WO | WO 2014/014913 | 1/2014 |
| WO | WO 2014/119165 | 8/2014 |
| WO | WO 2016/143572 | 9/2016 |

OTHER PUBLICATIONS

Choi et al., "$^{27}$Al NMR Chemical Shifts in Oxide Crystals: A First-Principles Study," *J. Phys. Chem. C*, 2009, 113 (9), pp. 3869-3873.

Lee et al., "Solid-state NMR Studies of Al-doped and Al2O3-coated LiCoO2," *Electrochimica Acta*, Nov. 30, 2004, vol. 50, Issues 2-3, pp. 491-494.

Han et al., "Understanding the Role of Temperature and Cathode Composition on Interface and Bulk: Optimizing Aluminum Oxide Coatings for Li-Ion Cathodes," *ACS Appl. Mater. Interfaces*, 2017, 9 (17), pp. 14769-14778.

Zhao et al., "Progress of Research on the Li-rich Cathode Materials xLi2MnO3(1-x)LiMO2(M+Co, Fe, Ni1/2Mn1/2 . . . ) for Li-ion Batteries," Journal of Inorganic Materials, vol. 26(7), pp. 673-679, Jul. 2011.

Lee et al., "Characteristics of LiCoO2 and its Precursor Synthesized by a Uniform Precipitation Method," Electrochemical and Solid-State Letters, 2010, vol. 13, No. 7, pp. A81-A84.

Kobayashi et al., "Study on the Crystal and Electronic Structures of the Layered Li2Mo3—LiMo2 Materials in Li De-Intercalation Process," *Photon Factory Activity Report*, 2012, vol. 29, No. 2011, 1 pp.

Giordano et al., "Metal Nitride and Metal Carbide Nanoparticles by a Soft Urea Pathway," *Chem. Mater.*, 2009, vol. 21, pp. 5136-5144.

Dou et al., "Synthesis and electrochemical properties of layered LiNi0.5-xMn0.5-xCo2xO2 for lithium-ion battery from nickel manganese cobalt precursor," *J Solid State Electrochem*, (2011), vol. 15, pp. 399-404.

Li, "Layered Oxides Li1+xM1-xO2 (M = Ni, Mn, Co, Al) as Cathode Materials for Rechargeable Lithium Ion Batteries," Dissertation, Submitted in partial fulfillment of the requirements for the degree of Doctor of Philosophy in Materials Science and Engineering in the Graduate School of Binghamton University State University of New York, Jul. 22, 2011, Published by UMI Dissertation Publishing, UMI No. 3474185, 158 pages.

Hu et al., "Ni, Mn—Co doped High-Voltage LiCoO2 Cathode Material for Lithium Ion Batteries," Chinese Journal of Inorganic Chemistry, 2015, vol. 31, Issue 1, pp. 159-165.

Rodrigues et al., "A novel coprecipitation method towards the synthesis of NiXMnXCo(1-2X)(OH)2 for the preparation of lithium metal oxides," *J Solid State Electrochem*, 2012, vol. 16, pp. 1121-1132.

Cho et al., "LiCoO2 Cathode Material that Does not Show a Phase Transition from Hexagonal to Monoclinic Phase," 2001, *Journal of the Electrochemical Society*, vol. 148, No. 10, pp. A1110-A1115.

(56) References Cited

OTHER PUBLICATIONS

Jung et al., "Enhanced Stability of LiCoO2 Cathodes in Lithium-Ion Batteries Using Surface Modification by Atomic Layer Deposition," 2010, *Journal of the Electrochemical Society*, vol. 157, No. 1, pp. A75-A81.
Koyama et al., "First principles study of dopant solubility and defect chemistry in Li CoO2," *J. Mater. Chem A.*, 2014, vol. 2, pp. 11235-11245.
Arunkumar et al., "Chemical and structural instability of the chemically delithiated (1-z) Li[Li$_{1/3}$Mn$_{2/3}$O$_2$ (z) Li[Co$_{1-y}$Ni$_y$]O$_2$ (O ≤ y ≤ 1 and 0 ≤ z ≤ 1) solid solution cathodes," *Journal of Materials Chemistry*, 2008, vol. 18, pp. 190-198.
Sun et al., "The Role of AlF3 Coatings in Improving Electrochemical Cycling of Li-Enriched Nickel-Manganese Oxide Electrodes for Li-Ion Batteries," *Adv. Mater.*, 2012, vol. 24, pp. 1192-1196.
Robertson et al., "Layered Li$_x$Mn$_{1-y}$Co$_y$O$_2$ Intercalation Electrodes—Influence of Ion Exchange on Capacity and Structure upon Cycling," *Chem. Mater.*, 2001, vol. 13, pp. 2380-2386.
Patoux et al., "Layered Manganese Oxide Intergrowth Electrodes for Rechargeable Lithium Batteries. 2. Substitution with Al," *Chem. Mater.*, 2005, vol. 17, pp. 1044-1054.
Myung et al., "Role of Alumina Coating on Li—Ni—Co—Mn—O Particles as Positive Electrode Material for Lithium-Ion Batteries," *Chem. Mater.*, 2005, vol. 17, pp. 3695-3704.
Wang et al., "Synthesis of Li$_2$MnO$_3$-stabilized LiCoO$_2$ cathode material by spray-drying method and its high voltage performance," *Journal of Alloys and Compounds*, 2015, vol. 626, pp. 228-233.
Zeng et al., "Cation ordering in Li[NixMnxCo(1-2x)]O-2-layered cathode materials: A nuclear magnetic resonance (NMR), pair distribution function, X-ray absorption spectroscopy, and electrochemical study," *Chemistry of Materials*, 2007, vol. 19. No. 25, pp. 6277-6289.
Zeng et al, "Investigation of the Structural Changes in Li[NiyMnyCo(1-2y)]O-2 (y=0.05) upon Electrochemical Lithium Deintercalation," *Chemistry of Materials*, 2010, vol. 22, No. 3, pp. 1209-1219.
Saadoune et al., "LiNi0.1Mn0.1Co0.8O2 electrode material: Structural changes upon lithium electrochemical extraction," *Electrochimica Acta*, 2010, vol. 55, No. 18, pp. 5180-5185.
Bentaleb et al., "On the LiNi0.2Mn0.2Co0.6O2 positive electrode material," *Journal of Power Sources*, 2010, vol. 195, No. 5, pp. 1510-1515.
Ben Kamel et al, "Local Structure and electrochemistry of LiNiyMnyCo1-2y)O2 electrode materials for Li-ion batteries," *Ionics*, 2008, vol. 14, No. 2, pp. 89-97.
Stoyanova et al., "High-Frequency Electron Paramagnetic Resonance Analysis of the Oxidation State and Local Structure of Ni and Mn Ions in Ni,Mn-Codoped LiCoO2," *Inorganic Chemistry*, 2010, vol. 49, No. 4, pp. 1932-1941.
Menetrier et al., "The insulator-metal transition upon lithium deintercalation from LiCoO2: electronic properties and Li-7 NMR Study," *Journal of Materials Chemistry*, 1999, vol. 9, No. 5, pp. 1135-1140.
Iddir et al., "Stability of Li- and Mn-Rich Layered-Oxide Cathodes within the First-Charge Voltage Plateau," *Journal of the Electrochemical Society*, 2016, vol. 163, No. 8, pp. A1784-A1789.
Seong-Min Bak et al, "Structural Changes and Thermal Stability of Charged LiNixMnyCozO2 Cathode Materials Studied by Combined In Situ Time-Resolved XRD and Mass Spectroscopy," *ACS Appl. Mater. Interfaces*, 2014, vol. 6, pp. 22594-22601.
Nam et al. "Ammonia-free coprecipitation synthesis of a Ni—Co—Mn hydroxide precursor for high-performance battery cathode materials," *Green Chemistry*, 2015. vol. 17, pp. 1127.
Xie et al., "An improved continuous co-precipitation method to synthesize LiNi0.80Co0.15Al0.05O2 cathode material," *Journal of Alloys and Compounds*, 2016, vol. 666, pp. 84-87.
Rouse et al., "Electrochemical Studies of Single Crystals of Lithiated Nickel Oxide," *Journal of the Electrochemical Society*, Feb. 1966, vol. 113, No. 2, pp. 184-190.
Jin et al., "Observation of Bulk Superconductivity in Na$_x$CoO$_2$•yH$_2$O and Na$_x$CoO$_2$•yD$_2$O Powder and Single Crystals," *Phys Rev Lett*, 2008, vol. 91, Issue 21, id. 217001, 4 pages.

Franger et al., "Chemistry and Electrochemistry of Low-Temperature Manganese Oxides as Lithium Intercalation Compounds," *Journal of the Electrochemical Society*, 2000, vol. 147, No. 9, pp. 3226-3230.
Lu et al., "Layered Li[Ni$_x$Co$_{1-2x}$Mn$_x$]O$_2$ Cathode Materials for Lithium-Ion Batteries," *Electrochemical and Solid-State Letters*, 2001, vol. 4, No. 12, pp. A200-A203.
Shinova et al., "Cationic distribution and electrochemical performance of LiCo$_{1/3}$Ni$_{1/3}$Mn$_{1/3}$O$_2$ electrodes for lithium-ion batteries," 2008, *Solid State Ionics*, vol. 179, pp. 2198-2208.
Qian et al., "Lithium Lanthanum Titanium Oxides: A Fast Ionic Conductive Coating for Lithium-Ion Battery Cathodes," *Chemistry of Materials*, 2012, 24 (14), pp. 2744-2751.
Reddy et al., "Effects of LLTO coating on high temperature cycle life performance of LiMn2O4 cathode material,"Abstract #382, 2012, The Electrochemical Society, 2 pages.
Davison et al., "Low Cost, Novel Methods for Fabricating All-Solid-State Lithium Ion Batteries," A Major Qualifying Project Submitted to the Faculty of Worcester Polytechnic Institute, Apr. 23, 2012, 126 pages.
Lee et al., "The Effects of Li—La—Ti—O Coating on the Properties of Li[Ni0.3Co0.4Mn0.3]O2 Cathode Material," Journal of the Korean Institute of Electrical and Electronic Material Engineers, Oct. 2009, vol. 22, No. 10, pp. 890-896.
Lee et al., "The Effect of Coating Thickness on the Electrochemical Properties of a Li—La—Ti—O-coated Li[Ni0.3Co0.4Mn0.3]O2 Cathode," Bull. Korean Chem. Soc., 2010, vol. 31, No. 11, pp. 3233-3237.
Hu et al., "Enhanced electrochemical performance of LiMn2O4 cathode with a Li0.34La0.51TiO3-caoted layer," *RSC Advances*, 2015. vol. 5, pp. 17592-17600.
Fergus et al., "Recent Devleopments in Cathode Materials for Lithium Ion Batteries," *Journal of Power Sources*, Vo. 195, No. 4, 23010, pp. 939-954.
Gille G. et al., "Cathode Materials for Rechargeable Batteries-Preparation, Structure-Property Relationsships and Performance," *Solid State Ionics*, Vo. 148, No. 3-4, 2002, pp. 269-282.
Periasamy et al., "High Voltage and High Capacity Characteristics of LiNi1/3Co1/3Mn1/3O2 Cathodes for Lithium Battery Applications," *Int. J. Electrochecm Soc.*, vol. 2, 2007, pp. 689-699.
Manthiram Lab Highlights, "Passivation of Spinel Cathod Surface through Self-Segregarion of Iron," May 7, 2010.
Cerion Power, "Our Power Business," www.cerionenterprises.com/companies_and_applications/power, accessed Sep. 8, 2011.
ETV Motors, "High5ive advanced high-voltage cells," www.etvemotors.com/advanced-battery.htm, accessed Sep. 8, 2011.
Wolfenstine et al., US Army RDECOM, "High Cycle Life Cathode for High Voltage (5V) Lithium Ion Batteries."
Sullivan, "Safe High Voltage Cathode Materials for Pulsed Power Applications," Navy STTR FY2011A—Topic N11A-T035, www.navy.sbir.com/n11_A/nayst11-035.htm, accessed Sep. 8, 2011.
Xu, US Army RDECOM, "Electrolyte for Next Generation 5V Li-Ion Batteries."
Ghosh et al., "Block Copolymer Solid Battery Electrolyte with High Li-Ion Transference Number," *Journal of the Electrochemical Society*, 2010, vol. 157, No. 7, pp. A846-A849.
Abu-Lebdeh et al., High-Voltage Electrolytes Based on Adiponitrile for Li-Ion Batteries, *Journal of the Electrochemical Society*, 2009, vol. 156, No. 1, pp. A60-A65.
Jow et al., "High Voltage Electrolytes for Li-ion Batteries," U.S. Research Laboratory, Presentation, May 2011.
Lucht, University of Rhode Island, "Development of Electrolytes for Lithium-ion Batteries," Presentation, May 11, 2001.
Zhang et al, Argonne National Laboratory, Vehicle Technologies Program Annual Merit Review and Peer Evaluation Meeting, "High Voltage Electrolyte for Lithium Batteries," Presentation, Jun. 9-13, 2011.
David Howell, US Department of Energy, "Vehicle Technologies Program," 2011 Annual Merit Review and Peer Evaluation Meeting, Presentation, May 9-13, 2011.

(56) References Cited

OTHER PUBLICATIONS

Fey et al., Preparation and electrochemical properties of high-voltage cathode maters, LiMyNi0.5-yMn1.5O4 (M = Fe, Cu, Al, Mg; y = 0.0-0.4), *Journal of Power Sources*, 2003, vol. 115, pp. 332-345.

Kawai et al., "High-voltage lithium cathode materials," Journal of Power Sources, 1999, vols. 81-82, abstract only.

Huang et al., "Lithium cobalt phosphate: a high voltage lithium ion cathode material," Valence Technologies.

"Award Details," SBIR/STTR, www.sbir.gov/sbirsearch/detail/233700, accessed Sep. 8, 2011.

Ju et al., "LiCo1-xAlxO2 (0≤x≤0.05) cathode powders prepared from the nanosized Co1-xAlxOy precursor powders," *Materials Chemistry and Physics*, 112 (2008), pp. 536-541.

Wu et al., "Effect of Al3+ and F− Doping on the Irreversible Oxygen Loss from Layered Li[Li0.17Mn0.58Ni0.25]O2 Cathodes," *Electrochemical and Solid-State Letters*, 2007, vol. 10, No. 6, pp. A151-A154.

Li et al, "Effects of fluorine doping on structure, surface chemistry, and electrochemical performance of LiNi0.8Co0.15Al0.05O2," *Electrochimica Acta*, 2015, vol. 174, pp. 1122-1130.

Cho et al., "Exploring Lithium Deficiency in Layered Oxide Cathode for Li-Ion Battery," *Advanced Sustainable Systems*, 2017, 1700026, 10 pages.

Lee et al., "Surface modification of LiNi0.5Mn1.5O4 cathodes with ZnAl2O4 by a sol-gel method for lithium ion batteries," *Electrochimica Acta*, 2014, vol. 115, pp. 326-331.

Kim et al., "Effect of fluorine on Li[Ni1/3Co1/3Mn1/3]O2-zFz as lithium intercalation material," *Journal of Power Sources*, 2005, vol. 146, pp. 602-605.

Yue et al., "The enhanced electrochemical performance of LiNi0.6Co0.2Mn0.2O2 cathode materials by low temperature fluorine substitution," *Electrochimica Acta*, 2013, vol. 95, pp. 112-118.

Wang et al., "Effect of surface fluorine substitution on high voltage electrochemical performances of layered LiNi0.5Co0.2Mn0.3O2 cathode materials," *Applied Surface Science*, 2016, vol. 371, pp. 172-179.

Tang et al., "Synthesis and characterization of LiFePO4 coating with aluminum doped zinc oxide," *Trans. Nonferrous Met. Soc. China*, 2013, vol. 23, pp. 451-455.

Myung et al., "Functionality of Oxide Coating for Li[Li0.05Ni0.4Co0.15Mn0.4])2 as Positive Electrode Materials for Lithium-Ion Secondary Batteries," *J. Phys. Chem. C*, 2007, vol. 111, pp. 4061-4067.

Liu et al., "Investigation the electrochemical performance of Li1.2Ni0.2Mn0.6O2 cathode material with ZnAl2O4 coating for lithium ion batteries," *Journal of Alloys and Compounds*, 2016, vol. 685, pp. 523-532.

Kim et al., "Improvement of High-Voltage Cycling Behavior of Surface-Modified Li[Ni1/3Co1/3Mn1/3]O2 Cathodes by Fluorine Substitution for Li-Ion Batteries," *J. Electrochem. Soc.*, 2005, vol., 152, issue 9, pp. A1707-A1713.

Chen et al., "Role of surface coating on cathode materials for lithium-ion batteries," *Journal of Materials Chemistry*, 2010, 20, 7606-7612.

Wenbin, Luo, "Effect of Al, Mg and Mn—Mg Doping on the Structure, Electrochemistry and Thermal Stability of LiCoO2 and LiNi1/3Mn1/3Co1/3O2," China Doctoral Dissertations Full-text Database Engineering Technology Part II, Nov. 15, 2010. (Translation provided by MultiLing).

Xinran, Cui, "Preparation and Properties of Al(3+) Doped Lithium-rich Layered Cathode Material Li[Co0.3Li0.23Mn0.47]O2," China Doctoral Dissertations Full-text Database Engineering Technology Part II, Oct. 15, 2012. (Translation provided by MultiLing).

\* cited by examiner

CATHODE ACTIVE MATERIALS HAVING IMPROVED PARTICLE MORPHOLOGIES

PRIORITY

The present application is a division of U.S. patent application Ser. No. 15/804,106, entitled "Cathode Active Materials having Improved Particle Morphologies," filed on Nov. 6, 2017, which is a continuation of U.S. patent application Ser. No. 15/709,961, entitled "Cathode Active Materials having Improved Particle Morphologies," filed on Sep. 20, 2017, which claims the benefit under 35 U.S.C. § 119(e) of U.S. Provisional Patent Application Ser. No. 62/397,019, entitled "Cathode Active Materials Having Improved Morphologies," filed on Sep. 20, 2016. The content of each application is incorporated herein by reference in its entirety.

U.S. GOVERNMENT LICENSE RIGHTS

This invention was made with U.S. government support under WFO Proposal No. 85F59. This invention was made under a CRADA 1500801 between Apple Inc. and Argonne National Laboratory operated for the United States Department of Energy. The U.S. government has certain rights in the invention.

FIELD

This disclosure relates generally to batteries, and more particularly, to cathode active materials for batteries having improved particle morphologies.

BACKGROUND

A commonly-used type of rechargeable battery is a lithium battery, such as a lithium-ion or lithium-polymer battery. As battery-powered devices become increasingly small and more powerful, lithium batteries powering these devices need to store more energy in a smaller volume. Consequently, use of battery-powered devices may be facilitated by mechanisms for improving the volumetric energy densities of lithium batteries in the devices.

SUMMARY

In one aspect, this disclosure is directed to particles comprising a compound selected from the group consisting of Formula (I), Formula (IIa), Formula (IIIa), Formula (IVa), Formula (Va), Formula (VIa), Formula (VIIa), and Formula (VIIIa). Each of the particles has an average density greater than or equal to 90% of an ideal crystalline density of the particles. Formula (Ia) is $$Ni_xMn_yCo_zMe_\alpha O_\beta \qquad (I)$$

in which Me is selected from B, Na, Mg, Al, Si, K, Ca, Sc, Ti, V, Cr, Fe, Cu, Zn, Ga, Ge, Zr, Nb, Mo, Ru, Ag, In, and combinations thereof, $0 \le x \le 1$, $0 \le y \le 1$, $0 \le z < 1$, $x+y+z>0$, $0 \le \alpha \le 0.5$, $x+y+\alpha>0$, and $1 \le \beta \le 5$.

Formula (IIa) is $$M^2 O_g \qquad (IIa)$$

wherein $M^2$ is selected from Co, Mn, Ni, and a combination thereof, and $0.9 \le g \le 2.6$.

Formula (IIIa) is $$M^3_j M^4_{1-j} O_j \qquad (IIIa)$$

wherein $M^3$ is selected from Ti, Mn, Zr, Mo, Ru, and any combination thereof $M^4$ is selected from B, Na, Mg, Ti, Ca, V, Cr, Mn, Fe, Co, Ni, Cu, Zn, Al, Sc, Y, Ga, Zr, Ru, Mo, and any combination thereof, $0 \le i \le 1$, and $0.9 \le j \le 2.6$.

Formula (IVa) is $$Co_{1-l} M^5_l Al_m O_n \qquad (IVa)$$

wherein $M^5$ is B, Na, Mn, Ni, Mg, Ti, Ca, V, Cr, Fe, Cu, Zn, Al, Sc, Y, Ga, Zr, Mo, Ru, and any combination thereof, $0 < l < 0.50$, $0 \le m \le 0.05$, and $0.9 \le n \le 2.6$.

Formula (Va) is $$Co_{1-p} Mn_p M^6_q O_r \qquad (Va)$$

wherein $M^6$ is at least one element selected from the group consisting of B, Na, Mg, Ti, Ca, V, Cr, Fe, Co, Ni, Cu, Zn, Al, Sc, Y, Ga, Zr, Ru, and Mo, $0 < p \le 0.30$, $0 \le q \le 0.10$, and $0.9 \le r \le 2.6$.

Formula (VIa) is $$(v)[M^7 O_2] \cdot (1-v)[Co_{1-\sigma} M^8_\sigma O_2] \qquad (VIa)$$

wherein $M^7$ is one or more elements with an average oxidation state of 4+, $M^8$ is one or more monovalent, divalent, trivalent, and tetravalent elements, $0.01 \le v < 1.00$, $0.5 \le w \le 1$, and $0 \le \sigma \le 0.05$.

Formula (VIIa) is $$Ni_x M^9_y M^{10}_z O_\alpha \qquad (VIIa)$$

wherein $M^9$ is selected from Mn, Ti, Zr, Ge, Sn, Te, and any combination thereof, $M^{10}$ is selected from Mg, Be, Ca, Sr, Ba, Fe, Ni, Cu, Zn, and any combination thereof, $0.7 < x < 1$, $0 < y < 0.3$, $0 < z < 0.3$, $x+y+z=1$, and $0.9 \le \alpha \le 2.6$.

Formula (VIIIa) is $$M^{11}_\gamma Ni_{(1-\gamma)\delta} M^{12}_{(1-\gamma)\varepsilon} M^{13}_{(1-\gamma)\zeta} O_\eta \qquad (VIIIa)$$

wherein $M^{11}$ is selected from Mn, Ti, Ru, Zr, and any combination thereof, $M^{12}$ is selected from Mn, Ti, Zr, Ge, Sn, Te, and any combination thereof, $M^{13}$ is selected from Mg, Be, Ca, Sr, Ba, Fe, Ni, Cu, Zn, and any combination thereof, $0 \le \gamma \le 0.3$, $0.7 < \delta < 1$, $0 < \varepsilon < 0.3$, $0 < \zeta < 0.3$, $\delta+\varepsilon+\zeta=1$, and $0.9 \le \eta \le 2.6$.

In some variations, the particles include crystallites.

In another aspect, this disclosure is directed to a the particles in which a first portion have a mean particle size between 1 and 50 μm. In some variations, the first portion of particles has a mean particle size between 10 and 20 μm. In some variations, the particles include a second portion of particles having a mean particle size between 1 and 5 μm.

In another aspect, this disclosure is directed to particles formed of a compound selected from the group consisting of Formula (Ib), Formula (IIb), Formula (IIIc), Formula (IVb), Formula (Vb), Formula (Vc), Formula (Ve), Formula (Vg), Formula (Vh), Formula (VIb), Formula (VIIb), Formula (VIIc), and Formula (VIIIb).

Formula (Ib) is $$Li_{1+\gamma} Ni_x Mn_y Co_z Me_\alpha O_\beta \qquad (Ib)$$

in which Me is selected from B, Na, Mg, Al, Si, K, Ca, Sc, Ti, V, Cr, Fe, Cu, Zn, Ga, Ge, Zr, Nb, Mo, Ru, Ag, In, and combinations thereof; $-0.1 \le \gamma \le 1.0$; $0 \le x \le 1$; $0 \le y \le 1$; $0 \le z < 1$; $x+y+z>0$; $0 \le \alpha \le 0.5$; $x+y+\alpha>0$; and $1.9 \le \beta \le 3$.

Formula (IIb) is $$Li_h M^2 O_g \qquad (IIb)$$

wherein $M^2$=Co, Mn, Ni, and any combination thereof, $0.95 \le h \le 2$, and $2 \le g \le 3$.

Formula (IIIb) is $$(i)[Li_2 M^3 O_3] \cdot (1-i)[LiM^4 O_2] \qquad (IIIb)$$

wherein $M^3$ is one or more cations with an average oxidation state of 4+, $M^4$ is one or more cations with an average oxidation state of 3+, and $0 \leq i \leq 1$.
Formula (IIIc) is

  (IIIc)

wherein $M^3$ is one or more cations with an average oxidation state of 4+, $M^4$ is one or more cations, $0 \leq i \leq 1$, and $0 \leq k \leq 1$.
Formula (IVb) is $Li_oCo_{1-l}M^5_lAl_mO_n$ (IVb)

wherein $M^5$ is B, Na, Mn, Ni, Mg, Ti, Ca, V, Cr, Fe, Cu, Zn, Al, Sc, Y, Ga, Zr, Mo, Ru, and any combination thereof, $0.95 \leq o \leq 1.10$, $0 < l < 0.50$, $0 \leq m \leq 0.05$, and $1.95 \leq n \leq 2.60$.
Formula (Vb) is $Li_sCo_{1-p}Mn_pO_r$ (Vb)

wherein $0.95 \leq s \leq 1.10$, $0 \leq p \leq 0.10$, and $1.90 \leq r \leq 2.20$.
Formula (Vc) is $(p)[Li_2MnO_3] \cdot (1-p)[LiCoO_2]$ (Vc)

wherein $0 \leq p \leq 0.10$.
Formula (Ve) is $(t)[Li_2MnO_3] \cdot (1-t)[Li_{(1-u)}Co_{(1-u)}Mn_uO_2]$ (Ve)

wherein $0 < t \leq 0.30$ and $0 \leq u \leq 0.10$.
Formula (Vg)

$Li_sCo_{1-p-q}Mn_pM^6_qO_r$ (Vg)

wherein $M^6$ is at least one element selected from the group consisting of B, Na, Mg, Ti, Ca, V, Cr, Fe, Co, Ni, Cu, Zn, Al, Sc, Y, Ga, Zr, Ru, and Mo, $0.95 \leq s \leq 1.30$, $0 < p \leq 0.30$, $0 \leq q \leq 0.10$, and $1.98 \leq r \leq 2.04$.
Formula (Vh) is $Li_sCo_{1-p-q}Mn_pAl_qO_r$ (Vh)

wherein $0.95 \leq s \leq 1.30$, $0 < p \leq 0.30$, $0 \leq q \leq 0.10$, and $1.98 \leq r \leq 2.04$.
Formula (VIb) is $(v)[Li_2M^7O_3] \cdot (1-v)[Li_aCo_{1-\sigma}M^8_\sigma O_2]$ (VIb)

wherein $M^7$ is one or more cations with an average oxidation state of 4+, $M^8$ is one or more monovalent, divalent, trivalent, and tetravalent cations, $0.01 \leq v < 1.00$, and $0.5 \leq w \leq 1$.
Formula (VIIb) is $Li_\beta Ni_x M^9_y M^{10}_z O_2$ (VIIb)

wherein $M^9$ is selected from Mn, Ti, Zr, Ge, Sn, Te, and a combination thereof, $M^{10}$ is selected from Mg, Be, Ca, Sr, Ba, Fe, Ni, Cu, Zn, and a combination thereof, $0.9 < \beta < 1.1$, $0.7 < x < 1$, $0 < y < 0.3$, $0 < z < 0.3$, and $x+y+z=1$.
Formula (VIIc) is $Li_\beta Ni_x Mn_y Mg_z O_2$ (VIIc)

wherein $0.9 < \beta < 1.1$, $0.7 < x < 1$, $0 < y < 0.3$, $0 < z < 0.3$, and $x+y+z=1$.
Formula (VIIIb) is $\gamma Li_2 M^{11}O_3 \cdot (1-\gamma)Li_\theta Ni_\delta M^{12}_\varepsilon M^{13}_\zeta O_2$ (VIIIb)

wherein $0 \leq \gamma \leq 0.3$, $M^{11}$ is selected from Mn, Ti, Ru, Zr, and any combination thereof, $M^{12}$ is selected from Mn, Ti, Zr, Ge, Sn, Te, and any combination thereof, $M^{13}$ is selected from Mg, Be, Ca, Sr, Ba, Fe, Ni, Cu, Zn, and any combination thereof, $0.9 < \theta < 1.1$, $0.7 < \delta < 1$, $0 < \varepsilon < 0.3$, $0 < \zeta < 0.3$, and $\delta+\varepsilon+\zeta=1$.

The particles have an average density greater than or equal to 90% of an ideal crystalline density of the particle. In some variations, the particles include crystallites.

In another aspect, this disclosure is directed to particles a first population The primary particles include a first portion having a mean particle size between 1 and 50 μm. In some variations, the first portion has a mean particle size between 10 and 20 μm. In some variations, the particles include a second portion having a mean particle size between 1 and 5 μm.

In another aspect, this disclosure is directed towards methods of manufacturing the aforementioned mixed-metal oxides and lithiated mixed-metal oxides. This disclosure is also directed to a cathode active material, a cathode, or a battery cell that includes the particles as described herein.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Figure 1A:
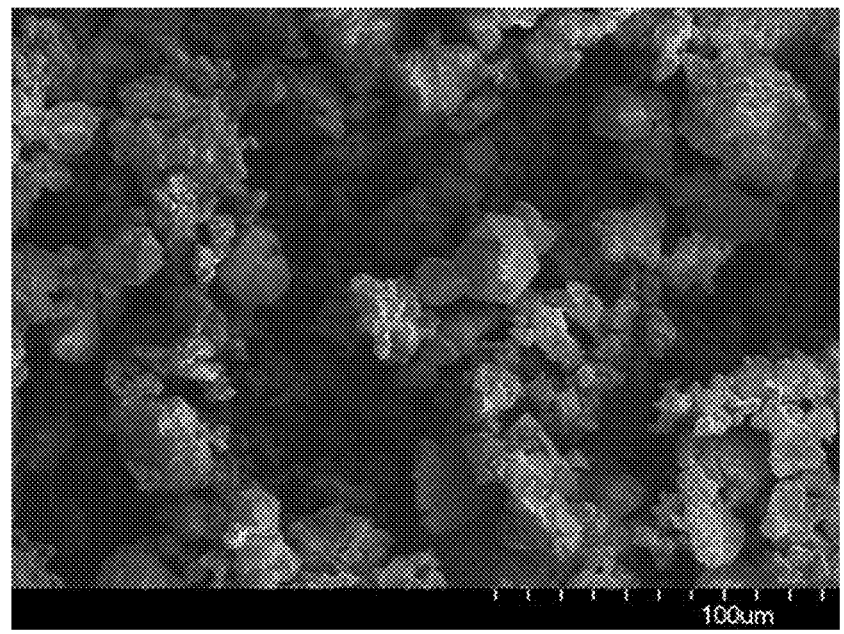
FIG. 1A is a scanning electron micrograph of particles of the mixed-metal oxide $Ni_{1/3}Mn_{1/3}Co_{1/3}O_\beta$ according to some illustrative embodiments.

Description of various embodiments will now be made with reference to the accompanying drawings. It should be understood that the following descriptions are not intended to limit the embodiments to any one preferred embodiment. To the contrary, it is intended to cover alternatives, modifications, and equivalents as can be included within the spirit and scope of the described embodiments as defined by the appended claims.

Conventional manufacturing of cathode active materials for lithium batteries rely on a reaction and calcination of lithium precursors (e.g., LiOH, $Li_2Co_3$, etc.) with metal precursors (e.g., oxides, hydroxides). Such manufacturing, which is typically conducted at high temperatures (i.e., >700° C.), produces powders having large portions of secondary particles. Secondary particles occur when solid, but smaller, primary particles bond together to form aggregates (i.e., during chemical or thermal processing). These aggregates exhibit morphologies that include voids and pores. Voids and pores reduce a density of the secondary particles relative to the primary particles from which they are formed. Voids and pores can also lower the strength of the secondary particles, thereby conferring a poor resistance to fracture.

Due to the voids and pores, secondary particles contain less material to store and release lithium ions during charge and discharge of a lithium battery. This impaired capability can negatively impact a volumetric energy density of the lithium battery. Moreover, during battery manufacturing, calendaring processes used to form layers of cathode active materials often utilize high pressures (i.e., >100 MPa). Such high pressures can induce severe particle fracture in secondary particles. Fractured secondary particles can increase a surface area of the cathode active material exposed to electrolyte fluid. As such, reaction of the cathode active material with the electrolyte fluid can be amplified, which in turn, increases a risk that the electrolyte fluid decomposes and generates gaseous by-products. Decomposition of the electrolyte fluid reduces performance of the lithium battery, and gas pressure therein can result in an unstable, unsafe state.

The cathode active materials described herein have improved particle morphologies that are substantially free of voids and pores. These morphologies have higher particulate densities and lower particulate surface areas when compared to conventional cathode active materials. Moreover, the cathode active materials may include a high proportion (i.e., >50% by frequency) of primary particles. Owing to at least these characteristics, the cathode active materials allow lithium batteries of higher volumetric energy density, lower gassing propensity, and enhanced safety. Also presented herein are methods for manufacturing cathode active materials with improved particle morphologies. These methods, which utilize wet solution processing, allow facile control of particle compositions and morphology.

In some variations, this disclosure is directed to particles (e.g., a powder) comprising a compound represented by Formula (Ia):

$$Ni_aMn_bCo_cM^1_dO_e \qquad (Ia)$$

In Formula (Ia), $M^1$ is selected from B, Na, Mg, Al, Si, K, Ca, Sc, Ti, V, Cr, Fe, Cu, Zn, Ga, Ge, Zr, Nb, Mo, Ru, Ag, In, and any combination thereof; $0 \le a \le 1$; $0 \le b \le 1$; $0 \le c \le 1$; $a+b+c>0$; $0 \le d \le 0.5$; $a+b+d>0$; and $1 \le e \le 5$. Compounds of Formula (Ia) include at least one of Ni, Mn, or Co (i.e., $a+b+c>0$). Moreover, the compounds include at least one of Ni, Mn, or $M^1$ (i.e., $a+b+d>0$).

In other variations, this disclosure is directed to particles (e.g., a powder) comprising a compound represented by Formula (Ib):

$$Li_{1+f}Ni_aMn_bCo_cM^1_dO_e \qquad (Ib)$$

It will be appreciated that the lithiated mixed-metal oxides may be prepared using the mixed-metal oxides associated with Formula (Ia), as will be discussed below. In Formula (Ib), $M^1$ is selected from B, Na, Mg, Al, Si, K, Ca, Sc, Ti, V, Cr, Fe, Cu, Zn, Ga, Ge, Zr, Nb, Mo, Ru, Ag, In, and combinations thereof; $0.1 \le f \le 1.0$; $0 \le a \le 1$; $0 \le b \le 1$; $0 \le c \le 1$; $a+b+c>0$; $0 \le d \le 0.5$; $a+b+d>0$; and $1.9 \le e \le 3$. Compounds of Formula (Ib) include at least one of Ni, Mn, or Co (i.e., $a+b+c>0$). Moreover, the compounds include at least one of Ni, Mn, or $M^1$ (i.e., $a+b+d>0$). As used herein, all compounds referenced for the lithiated mixed-metal oxides represent those of as-prepared materials (i.e., "virgin" materials) unless otherwise indicated. Such compounds have not yet been exposed to additional chemical processes, such as de-lithiation and lithiation during, respectively, charging and discharging. In some instances, $0 \le f \le 0.5$. In some instances, $1.9 \le e \le 2.7$. In further instances, $1.9 \le e \le 2.1$.

In some instances, $0 \le f \le 1.0$ and $d=0$. In these instances, no content associated with $M^1$ is present in the particles. Further, in some instances, $d=0$ and $f \ge 0.20$. In some instances, $d=0$ and $f \ge 0.40$. In some instances, $d=0$ and $f \ge 0.60$. In some instances, $d=0$ and $f \ge 0.80$. In some instances, $d=0$ and $f \le 0.80$. In some instances, $d=0$ and $f \le 0.60$. In some instances, $d=0$ and $f \le 0.40$. In some instances, $d=0$ and $f \le 0.20$. In some instances, $d=0$ and $e \ge 2.20$. In some instances, $d=0$ and $e \ge 2.40$. In some instances, $d=0$ and $e \ge 2.60$. In some instances, $d=0$ and $e \ge 2.80$. In some instances, $d=0$ and $e \le 2.80$. In some instances, $d=0$ and $e \le 2.60$. In some instances, $d=0$ and $e \le 2.40$. In some instances, $d=0$ and $e \le 2.20$. It will be understood that, in the aforementioned instances, the boundaries of f and e can be combined in any variation as above.

In some instances, $M^1$ includes one or more cations with an average oxidation state of 4+, i.e., $M^1_1$. $M^1$ also includes one or more cations with an oxidation state of 3+, i.e., $M^1_2$. $M^1_1$ is selected from Ti, Mn, Zr, Mo, and Ru and may be any combination thereof. $M^1_2$ is selected from Mg, Ca, V, Cr, Fe, Cu, Zn, Al, Sc, Y, Ga, and Zr and may be any combination thereof. A stoichiometric content associated with $M^1_1$, i.e., $d_1$, and a stoichiometric content associated with $M^1_2$, i.e., $d_2$, equals d (i.e., $d_1+d_2=d$). In these instances, $a+b+c+d_1+d_2=1$. Further, in some instances, $d_1 \geq 0.1$. In some instances, $d_1 \geq 0.2$. In some instances, $d_1 \geq 0.3$. In some instances, $d_1 \geq 0.4$. In some instances, $d_1 \leq 0.1$. In some instances, $d_1 \leq 0.2$. In some instances, $d_1 \leq 0.3$. In some instances, $d_1 \leq 0.4$. It will be understood that, in the aforementioned instances, the boundaries of $d_1$ can be combined in any variation as above.

In some instances, $-0.05 \leq f \leq 0.10$; $M^1=Al$; $0 \leq d \leq 0.05$; $a+b+c=1$; $0<a+b<0.5$; and $1.95 \leq e \leq 2.6$. In further instances, $0.01 \leq d \leq 0.03$. In still further instances, $0.02 \leq d \leq 0.03$. In instances where $d \neq 0$ (i.e., aluminum is present), a distribution of aluminum within each particle may be uniform or may be biased to be proximate to a surface of each particle. Other distributions are possible.

In some instances, $-0.05 \leq f \leq 0.10$; $d=0$; $a=0$, $b+c=1$; and $1.9 \leq e \leq 2.2$. Further, in some instances, $0.0 \leq f \leq 0.10$. In some instances, $0.0 \leq f \leq 0.05$. In some instances, $0.01 \leq f \leq 0.05$ and $0.02 \leq b \leq 0.05$. In some instances, $0.01 \leq f \leq 0.05$ and $b=0.04$.

In some variations, this disclosure is directed to particles (e.g., a powder) comprising a compound represented by Formula (IIa):

$$M^2O_g \qquad (IIa)$$

wherein $M^2$=Co, Mn, Ni, and any combination thereof; and $0.9 \leq g \leq 2.6$. In some variations, $0.9 \leq g \leq 1.1$. In some variations, $g=1$. In some variations, $1.4 \leq g \leq 1.6$. In some variations, $g=1.5$. In some variations, $1.9 \leq g \leq 2.1$. In some variations, $g=2$. In some variations, $2.4 \leq g \leq 2.6$. In some variations, $g=2.5$.

In other variations, this disclosure is directed to particles (e.g., a powder) comprising a compound represented by Formula (IIb):

$$Li_hM^2O_g \qquad (IIb)$$

wherein $M^2$=Co, Mn, Ni, and any combination thereof, $0.95 \leq h \leq 2$, and $2 \leq g \leq 3$. In some variations, $1 \leq h \leq 2$. In some variations, $1.20 \leq h$. In some variations, $1.40 \leq h$. In some variations, $1.60 \leq h$. In some variations, $1.80 \leq h$. In some variations, $h \leq 1.8$. In some variations, $h \leq 1.6$. In some variations, $h \leq 1.4$. In some variations, $h \leq 1.2$. In some variations, $h \leq 1.8$. Further, in some variations, $2.2 \leq g$. In some variations, $2.4 \leq g$. In some variations, $2.6 \leq g$. In some variations, $2.8 \leq g$. In some variations, $g \leq 2.8$. In some variations, $g \leq 2.6$. In some variations, $g \leq 2.4$. In some variations, $g \leq 2.2$. It will be understood that the boundaries of h and g can be combined in any variation as above.

In some variations, this disclosure is directed to particles (e.g., a powder) comprising a compound represented by Formula (IIIa):

$$M^3_iM^4_{1-i}O_j \qquad (IIIa)$$

wherein $M^3$ is selected from Ti, Mn, Zr, Mo, Ru, and any combination thereof; $M^4$ is selected from B, Na, Mg, Ti, Ca, V, Cr, Mn, Fe, Co, Ni, Cu, Zn, Al, Sc, Y, Ga, Zr, Ru, Mo, and any combination thereof; $0 \leq i \leq 1$; and $0.9 \leq j \leq 2.6$. In some variations, $M^3$ has an average oxidation state of 4+(i.e., tetravalent). In some variations, $M^4$ has an average oxidation state of 3+(i.e., trivalent). In some variations, $0<i<1$. In specific variations, $M^3$ is Mn. In specific variations, $M^4$ is Co. In specific variations, $M^4$ is a combination of Co and Mn. In further variations, a proportion of Co is greater than a proportion of Mn in the combination of Co and Mn.

In some variations, $1.4 \leq j \leq 2.1$. In some variations, $1.5 \leq j \leq 2.0$. In some variations, $1.6 \leq j \leq 1.9$. In some variations, $0.9 \leq j \leq 1.1$. In some variations, $j=1$. In some variations, $1.4 \leq j \leq 1.6$. In some variations, $j=1.5$. In some variations, $1.9 \leq j \leq 2.1$. In some variations, $j=2$. In some variations, $2.4 \leq j \leq 2.6$. In some variations, $j=2.5$.

In other variations, this disclosure is directed to particles (e.g., a powder) comprising a compound represented by Formula (IIIb):

$$(i)[Li_2M^3O_3].(1-i)[LiM^4O_2] \qquad (IIIb)$$

wherein $M^3$ is one or more cations with an average oxidation state of 4+(i.e., tetravalent), $M^4$ is one or more cations with an average oxidation state of 3+(i.e., trivalent), and $0 \leq i \leq 1$. In some variations, $M^3$ is selected from Ti, Mn, Zr. Mo, Ru, and a combination thereof. In specific variations, $M^3$ is Mn. In some variations, $M^4$ is selected from B, Na, Mg, Ti, Ca, V, Cr, Mn, Fe, Co, Ni, Cu, Zn, Al, Sc, Y, Ga, Zr, Ru, Mo and a combination thereof. In specific variations, $M^4$ is Co. In specific variations, $M^4$ is a combination of Co and Mn. In further variations, a proportion of Co is greater than a proportion of Mn in the combination of Co and Mn. In variations where $M^4$ includes cobalt, cobalt may be a predominant transition-metal constituent which allows high voltage, and high volumetric energy density for cathode active materials employed in lithium-ion batteries.

In still other variations, this disclosure is directed to particles (e.g., a powder) comprising a compound represented by Formula (IIIc):

$$(i)[Li_2M^3O_3].(1-i)[Li_{1-k}M^4O_2] \qquad (IIIc)$$

wherein $M^3$ is one or more cations with an average oxidation state of 4+(i.e., tetravalent), $M^4$ is one or more cations, $0 \leq i \leq 1$, and $0 \leq k \leq 1$. In some variations, $M^3$ is selected from Ti, Mn, Zr, Mo, Ru, and a combination thereof. In specific variations, $M^3$ is Mn. In some variations, $M^4$ is selected from B, Na, Mg, Ti, Ca, V, Cr, Mn, Fe, Co, Ni, Cu, Zn, Al, Sc, Y, Ga, Zr, Ru, Mo, and any combination thereof. In specific variations, $M^4$ is Co. In specific variations, $M^4$ is a combination of Co and Mn. In further variations, a proportion of Co is greater than a proportion of Mn in the combination of Co and Mn. In variations where $M^4$ includes cobalt, cobalt may be a predominant transition-metal constituent which allows high voltage, and high volumetric energy density for cathode active materials employed in lithium-ion batteries.

In some variations, $0 \leq k \leq 0.16$. In some variations, $0 \leq k \leq 0.14$. In some variations, $0 \leq k \leq 0.12$. In some variations, $0 \leq k \leq 0.10$. In some variations, $0 \leq k \leq 0.08$. In some variations, $0 \leq k \leq 0.06$. In some variations, $0 \leq k \leq 0.04$. In some variations, $0 \leq k \leq 0.02$. In some variations, $k=0.15$. In some variations, $k=0.14$. In some variations, $k=0.13$. In some variations, $k=0.12$. In some variations, $k=0.11$. In some variations, $k=0.10$. In some variations, $k=0.09$. In some variations, $k=0.08$. In some variations, $k=0.07$. In some variations, $k=0.06$. In some variations, $k=0.05$. In some variations, $k=0.04$. In some variations, $k=0.03$. In some variations, $k=0.02$. In some variations, $k=0.01$.

In some variations, this disclosure is directed to particles (e.g., a powder) comprising a compound represented by Formula (IVa):

$$Co_{1-l}M^5_lAl_mO_2 \qquad (IVa)$$

wherein $M^5$ is B, Na, Mn, Ni, Mg, Ti, Ca, V, Cr, Fe, Cu, Zn, Al, Sc, Y, Ga, Zr, Mo, Ru, and any combination thereof; $0<l<0.50$; $0\leq m\leq 0.05$; and $0.9\leq n\leq 2.6$. In some variations, $M^5$ is Mn, Ni, and any combination thereof.

In some variations, $1.4\leq n\leq 2.1$. In some variations, $1.5\leq n\leq 2.0$. In some variations, $1.6\leq n\leq 1.9$. In some variations, $0.9\leq n\leq 1.1$. In some variations, $n=1$. In some variations, $1.4\leq n\leq 1.6$. In some variations, $n=1.5$. In some variations, $1.9\leq n\leq 2.1$. In some variations, $n=2$. In some variations, $2.4\leq n\leq 2.6$. In some variations, $n=2.5$.

In some variations, $0.01\leq m\leq 0.03$. In some variations, $0.001\leq m\leq 0.005$. In some variations, $0.002\leq m\leq 0.004$. In some variations, $m=0.003$. In some variations, $0.02\leq m\leq 0.03$. In variations of Formula (IVa) where m 0 (i.e., aluminum is present), a distribution of aluminum within the particle may be uniform or may be biased to be proximate to a surface of the particle. Other distributions of aluminum are possible. In some variations, Al is at least 500 ppm. In some variations, Al is at least 750 ppm. In some variations, Al is at least 900 ppm. In some variations, Al is less than or equal to 2000 ppm. In some variations, Al is less than or equal to 1500 ppm. In some variations, Al is less than or equal to 1250 ppm. In some variations, Al is approximately 1000 ppm. In an optional alternative, the compound can be expressed as $Co_{1-l}M^5_lO_n$ and Al expressed in ppm.

In some variations, $0.9\leq n\leq 1.1$. In some variations, $n=1$. In some variations, $1.4\leq n\leq 1.6$. In some variations, $n=1.5$. In some variations, $1.9\leq n\leq 2.1$. In some variations, $n=2$. In some variations, $2.4\leq n\leq 2.6$. In some variations, $n=2.5$. In some variations, $1.4\leq n\leq 2.1$. In some variations, $1.5\leq n\leq 2.0$. In some variations, $1.6\leq n\leq 1.9$.

In other variations, this disclosure is directed to particles (e.g., a powder) comprising a compound represented by Formula (IVb):

$$Li_oCo_{1-l}M^5_lAl_mO_n \qquad \text{(IVb)}$$

wherein $M^5$ is B, Na, Mn, Ni, Mg, Ti, Ca, V, Cr, Fe, Cu, Zn, Al, Sc, Y, Ga, Zr, Mo, Ru, and any combination thereof; $0.95\leq o\leq 1.10$; $0<l<0.50$; $0\leq m\leq 0.05$; and $1.95\leq n\leq 2.60$. In some variations, $M^5$ is Mn, Ni, and any combination thereof.

In some variations, $0.01\leq m\leq 0.03$. In some variations, $0.001\leq m\leq 0.005$. In some variations, $0.002\leq m\leq 0.004$. In some variations, $m=0.003$. In some variations, $0.02\leq m\leq 0.03$. In variations of Formula (IVb) where $m\neq 0$ (i.e., aluminum is present), a distribution of aluminum within the particle may be uniform or may be biased to be proximate to a surface of the particle. Other distributions of aluminum are possible. In some variations, Al is at least 500 ppm. In some variations, Al is at least 750 ppm. In some variations, Al is at least 900 ppm. In some variations, Al is less than or equal to 2000 ppm. In some variations, Al is less than or equal to 1500 ppm. In some variations, Al is less than or equal to 1250 ppm. In some variations, Al is approximately 1000 ppm. In additional variations of Formula (IVb), $1.02\leq o\leq 1.05$ and $0.02\leq l\leq 0.05$. In further variations of Formula (4b), $1.03\leq o\leq 1.05$ and $l=0.04$. It will be recognized that the components as described above can be in any combination. In some instances, when Al is expressed in ppm, in one aspect, the compound can be represented as $Li_oCo_{1-l}M^5_lO_n$ and the amount of Al can be represented as Al in at least a quantity in ppm, as described herein.

The various compounds of Formulae (IIb), (IIIb), (IIIc), and (IVb) can include $Mn^{4+}$. Without wishing to be limited to any theory or mode of action, incorporating $Mn^{4+}$ can improve a stability of oxide under high voltage charging (e.g., 4.5V) and can also help maintain an $R\overline{3}m$ crystal structure (i.e., the $\alpha$-NaFeO$_2$ structure) when transitioning through a 4.1-4.3V region (i.e., during charging and discharging).

In some variations, this disclosure is directed to particles (e.g., a powder) comprising a compound represented by Formula (Va):

$$Co_{1-p}Mn_pM^6_qO_r \qquad \text{(Va)}$$

wherein $M^6$ is at least one element selected from the group consisting of B, Na, Mg, Ti, Ca, V, Cr, Fe, Co, Ni, Cu, Zn, Al, Sc, Y, Ga, Zr, Ru, and Mo; $0<p\leq 0.30$; $0\leq q\leq 0.10$; and $0.9\leq r\leq 2.6$. In some variations, $q=0$. In some variations, $M^6$ is Al.

In some variations, $1.4\leq r\leq 2.1$. In some variations, $1.5\leq r\leq 2.0$. In some variations, $1.6\leq r\leq 1.9$. In some variations, $0.9\leq r\leq 1.1$. In some variations, $r=1$. In some variations, $1.4\leq r\leq 1.6$. In some variations, $r=1.5$. In some variations, $1.9\leq r\leq 2.1$. In some variations, $n=r$. In some variations, $2.4\leq r\leq 2.6$. In some variations, $r=2.5$.

In other variations, this disclosure is directed to particles (e.g., a powder) comprising a compound represented by Formula (Vb):

$$Li_sCo_{1-p}Mn_pO_r \qquad \text{(Vb)}$$

wherein $0.95\leq s\leq 1.10$, $0\leq p\leq 0.10$, and $1.90\leq r\leq 2.20$. In some variations, $0<p\leq 0.10$. In some variations, $0.98\leq s\leq 1.01$. In some variations of Formula (Vb), $0.98\leq s\leq 1.01$ and $p=0.03$. In some variations of Formula (Vb), $1.00\leq s\leq 1.05$. In some variations, the disclosure is directed to a compound represented by Formula (Vb), wherein $0.95\leq s\leq 1.05$ and $0.02\leq\beta\leq 0.05$. In a further aspect, the disclosure is directed to a compound represented by Formula (Vb), wherein $0.95\leq s\leq 1.05$ and $p=0.04$. In some variations, $p=0.03$. In further variations of Formula (Vb), $1.01\leq s\leq 1.05$ and $0.02\leq\beta\leq 0.05$. In still further variations of Formula (Vb), $1.01\leq s\leq 1.05$ and $p=0.04$. In some variations of Formula (Vb), $1.00<s\leq 1.10$. In other variations of Formula (Vb), $1.00\leq s\leq 1.05$. In a further aspect, the disclosure is directed to a compound represented by Formula (Vb), wherein $0.98\leq s\leq 1.01$, $p=0.03$, and $r=2$.

It will be appreciated that s represents a molar ratio of lithium content to total transition-metal content (i.e., total content of Co and Mn). In various aspects, increasing lithium content can increase capacity, improve stability, increase gravimetric density of particles comprising the compound, increase particle density, and/or increase particle strength of the cathode active material. In various aspects, decreasing lithium content can increase capacity, improve stability, increase gravimetric density of particles comprising the compound, increase particle density, and/or increase particle strength of the cathode active material.

In some variations, the compound of Formula (Vb) may be represented as a solid solution of two phases, i.e., a solid solution of $Li_2MnO_3$ and $LiCoO_2$. In these variations, the compound may be described according to Formula (Vc):

$$(p)[Li_2MnO_3]\cdot(1-p)[LiCoO_2] \qquad \text{(Vc)}$$

where Mn is a cation with an average oxidation state of 4+ (i.e., tetravalent) and Co is a cation with an average oxidation state of 3+ (i.e., trivalent). A more compact notation for Formula (Vc) is given below:

$$Li_{1+p}Co_{1-p}Mn_pO_{2+p} \qquad \text{(Vd)}$$

In Formula (Vd), p can describe both Mn and Co. Due to differing valences between Mn and Co, the inclusion of Mn may influence a lithium content and an oxygen content of the compound.

Referring back to Formula (Vb), 'p' can be 0≤p≤0.10. In such variations, the lithium content can be from 1 to 1.10 (i.e., 1+p), and the oxygen content can be from 2 to 2.10 (i.e., 2+p). However, the compounds disclosed herein have lithium contents and oxygen contents that may vary independently of p. For example, and without limitation, the lithium and oxygen contents may vary from stoichiometric values due to synthesis conditions deliberately selected by those skilled in the art. As such, subscripts in Formulas (Vc) and (Vd) are not intended as limiting on Formula (Vb), i.e., s is not necessarily equal to 1+p, and r is not necessarily equal 2+p. It will be appreciated that one or both of the lithium content and the oxygen content of compounds represented by Formula (Vb) can be under-stoichiometric (i.e., s<1+p; r<2+p) or over-stoichiometric (i.e., s>1+l; r>2+p) relative to the stoichiometric values of Formula (Vd).

In some variations, the compound of Formula (Vb) may be represented as a solid solution of two phases, i.e., a solid solution of $Li_2MnO_3$ and $LiCoO_2$. In these variations, the compound may be described according to Formula (Ve):

$$(t)[Li_2MnO_3].(1-t)[Li_{(1-u)}Co_{(1-u)}Mn_uO_2] \quad (Ve)$$

where Mn is a cation with an average oxidation state of 4+(i.e., tetravalent) and Co is a cation with an average oxidation state of 3+(i.e., trivalent). A unified notation for Formula (Ve) is given below:

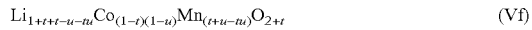
$$Li_{1+t+t-u-tu}Co_{(1-t)(1-u)}Mn_{(t+u-tu)}O_{2+t} \quad (Vf)$$

In Formula (Vf), t and u can describe both Mn and Co. Without wishing to be held to a particular mechanism or mode of action, because of differing valences between Mn and Co, inclusion of Mn may influence lithium content and oxygen content of the compound.

Comparing Formulas (Vb) and (Vf) shows s=1+t−u−tu, p=t+u−tu, r=2+t. In compounds represented by Formula V(f), the lithium content can be any range described herein for Formula (Vb). In some variations, Li can be from 0.95 to 1.10. In some variations, oxygen content can be from 2 to 2.20.

In other variations, this disclosure is directed to particles (e.g., a powder) comprising a compound represented by Formula (Vg):

$$Li_sCo_{1-p-q}Mn_pM^6_qO_r \quad (Vg)$$

wherein 0.95≤s≤1.30, 0<p≤0.30, 0≤q≤0.10, and 1.98≤r≤2.04, and $M^6$ is at least one element selected from the group consisting of B, Na, Mg, Ti, Ca, V, Cr, Fe, Co, Ni, Cu, Zn, Al, Sc, Y, Ga, Zr, Ru, and Mo. The compound of Formula (Vg) is single phase. The compound can have a trigonal R3̄m crystal structure. In further variations, 0.98≤s≤1.16 and 0<p≤0.16. In some variations 0.98≤s≤1.16, 0<p≤0.16, and 0<q≤0.05.

In other variations, this disclosure is directed to particles (e.g., a powder) comprising a compound represented by Formula (Vh):

$$Li_sCo_{1-p-q}Mn_pAl_qO_r \quad (Vh)$$

wherein 0.95≤s≤1.30, 0<p≤0.30, 0≤q≤0.10, and 1.98≤r≤2.04. In some variations, 0.96≤s≤1.04, 0<p≤0.10, 0≤q≤0.10, and 1.98≤r≤2.04. In some variations, the compounds represented by Formula (Vh) have 0.98≤s≤1.01, 0.02≤p≤0.04, and 0≤q≤0.03. The compound of Formula (Vh) is a single phase. The compound can have trigonal R3̄m crystal structure.

In other variations, the disclosure is directed to particles comprising a compound represented by Formula (VIa):

$$(v)[M^7O_2].(1-v)[Co_{1-\sigma}M^8_\sigma O_2] \quad (VIa)$$

wherein $M^7$ is one or more elements with an average oxidation state of 4+(i.e., tetravalent); $M^8$ is one or more monovalent, divalent, trivalent, and tetravalent elements; 0.01≤v<1.00, and 0≤σ≤0.05. In some variations, $M^7$ is selected from Mn, Ti, Zr, Ru, and a combination thereof. In some variations, $M^8$ is selected from B, Na, Mg, Ti, Ca, V, Cr, Mn, Fe, Co, Ni, Cu, Zn, Al, Sc, Y, Ga, Zr, Ru, Mo and a combination thereof. In some variations, $M^7$ is Mn. In some variations, $M^8$ is Al.

In some embodiments, 0.01≤v≤0.50. In some embodiments, 0.01≤v<0.50. In some embodiments, 0.01≤v<0.30. In some embodiments, 0.01≤v<0.10. In some embodiments, 0.01≤v<0.05. In some variations, 0<σ≤0.05. In some variations, 0<σ≤0.03. In some variations, 0<σ≤0.02. In some variations, 0<σ≤0.01. In some variations, 0.01≤v<0.05, and 0<σ≤0.05.

In some variations, Al is at least 500 ppm. In some variations, Al is at least 750 ppm. In some variations, Al is at least 900 ppm. In some variations, Al is less than or equal to 2000 ppm. In some variations, Al is less than or equal to 1500 ppm. In some variations, Al is less than or equal to 1250 ppm. In some variations, Al is less than or equal to 1000 ppm. In some variations, Al is less than or equal to 900 ppm. In some variations, Al is less than or equal to 800 ppm. In some variations, Al is less than or equal to 700 ppm. In some variations, Al is less than or equal to 600 ppm. In some instances, when $M^8$ (e.g., Al) is expressed in ppm, in optional variations, the compound can be represented as $(v)[Li_2M^7O_3].(1-v)[Li_\alpha Co_w O_2]$ and the amount of $M^8$ can be represented as $M^8$ in at least a quantity in ppm, as otherwise described above. In some embodiments, 0.5≤w≤1. In some embodiments, 0.8≤w≤1. In some embodiments, 0.96≤w≤1. In some embodiments, 0.99≤w≤1. In some embodiments, w is 1.

In other variations, this disclosure is directed to particles comprising a compound represented by Formula (VIb):

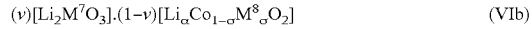
$$(v)[Li_2M^7O_3].(1-v)[Li_\alpha Co_{1-\sigma}M^8_\sigma O_2] \quad (VIb)$$

wherein $M^7$ is one or more elements with an average oxidation state of 4+(i.e., tetravalent); $M^8$ is one or more monovalent, divalent, trivalent, and tetravalent elements; 0.95≤α<0.99; 0.01≤v<1.00, and 0.5≤w≤1, and 0≤σ≤0.05. In some variations, $M^7$ is selected from Mn, Ti, Zr, Ru, and a combination thereof. In some variations, $M^8$ is selected from B, Na, Mg, Ti, Ca, V, Cr, Mn, Fe, Co, Ni, Cu, Zn, Al, Sc, Y, Ga, Zr, Ru, Mo and a combination thereof. In some variations, $M^7$ is Mn. In some variations, $M^8$ is Al.

In some embodiments, 0.01≤v≤0.50. In some embodiments, 0.01≤v<0.50. In some embodiments, 0.01≤v<0.30. In some embodiments, 0.01≤v<0.10. In some embodiments, 0.01≤v<0.05. In some variations, 0<α≤0.05. In some variations, 0<σ≤0.03. In some variations, 0<σ≤0.02. In some variations, 0<σ≤0.01. In some variations, 0.95≤α<0.99, 0.01≤v<0.05, 0.96≤w<1, and 0<σ≤0.05.

In some variations, $M^8$ (e.g., Al) is at least 500 ppm. In some variations, $M^8$ (e.g., Al) is at least 750 ppm. In some variations, $M^8$ (e.g., Al) is at least 900 ppm. In some variations, $M^8$ (e.g., Al) is less than or equal to 2000 ppm. In some variations, $M^8$ (e.g., Al) is less than or equal to 1500 ppm. In some variations, $M^8$ (e.g., Al) is less than or equal to 1250 ppm. In some variations, $M^8$ (e.g., Al) is less than or equal to 1000 ppm. In some variations, $M^8$ (e.g., Al) is less than or equal to 900 ppm. In some variations, $M^8$ (e.g., Al) is less than or equal to 800 ppm. In some variations, $M^8$ (e.g., Al) is less than or equal to 700 ppm. In some variations, $M^8$ (e.g., Al) is less than or equal to 600 ppm. In some instances, when $M^8$ (e.g., Al) is expressed in ppm, the compound can be represented as $(v)[Li_2M^7O_3].(1-v)[Li_\alpha Co_w O_2]$ and the amount of $M^8$ can be represented as $M^8$ in at least a quantity in ppm, as otherwise described above. In some variations, $0.5 \leq w \leq 1$. In some variations, $0.8 \leq w \leq 1$. In some variations, $0.96 \leq w \leq 1$. In some variations, $0.99 \leq w \leq 1$. In some variations, w is 1.

In some variations, the disclosure is directed to a cathode active material for lithium ion batteries that includes a lithium nickel oxide ($LiNiO_2$) having one or more tetravalent metals selected from Mn, Ti, Zr, Ge, Sn, and Te and/or one or more divalent metals selected from Mg, Be, Ca, Sr, Ba, Fe, Ni, Cu, and Zn. In these materials, the trivalent Ni ion can serve as host to supply the capacity. Without wishing to be limited to any theory or mode of action, a tetravalent ion such as $Mn^{4+}$, and a divalent ion such as $Mg^{2+}$, can stabilize the structure and help Ni ion stay trivalent for typical layer $LiNiO_2$ oxide.

The lithium nickel oxide may also include a stabilizer component, $Li_2MeO_3$, in which Me is one or more elements selected from Mn, Ti, Ru, and Zr. Without wishing to be limited to any theory or mode of action, $Li_2MeO_3$ can stabilize a layered crystal structure and improve a reversible capability of the lithium nickel oxide in a voltage window of a lithium-ion cell. Representative examples of Me include Mn, Ti, Ru, Zr, and any combination thereof.

In some variations, this disclosure is directed to particles (e.g., a powder) comprising a compound represented by Formula (VIIa):

$$Ni_x M^9{}_y M^{10}{}_z O_\alpha \qquad (VIIa)$$

where $M^9$ is selected from Mn, Ti, Zr, Ge, Sn, Te, and any combination thereof; $M^{10}$ is selected from Mg, Be, Ca, Sr, Ba, Fe, Ni, Cu, Zn, and any combination thereof; $0.7<x<1$; $0<y<0.3$; $0<z<0.3$; $x+y+z=1$; and $0.9 \leq \alpha \leq 2.6$. In some variations of Formula (VIIa), $M^9$ is Mn and $M^{10}$ is Mg. In some variations of Formula (VIIa), $0.05<y<0.3$ and $0.05<z<0.3$.

In some variations, $1.4 \leq \alpha \leq 2.1$. In some variations, $1.5 \leq \alpha \leq 2.0$. In some variations, $1.6 \leq \alpha \leq 1.9$. In some variations, $0.9 \leq \alpha \leq 1.1$. In some variations, $\alpha=1$. In some variations, $1.4 \leq \alpha \leq 1.6$. In some variations, $\alpha=1.5$. In some variations, $1.9 \leq \alpha \leq 2.1$. In some variations, $\alpha=2$. In some variations, $2.4 \leq \alpha \leq 2.6$. In some variations, $\alpha=2.5$.

In other variations, this disclosure is directed to particles (e.g., a powder) comprising a compound represented by Formula (VIIb):

$$Li_\beta Ni_x M^9{}_y M^{10}{}_z O_2 \qquad (VIIb)$$

where $M^9$ is selected from Mn, Ti, Zr, Ge, Sn, Te, and a combination thereof; $M^{10}$ is selected from Mg, Be, Ca, Sr, Ba, Fe, Ni, Cu, Zn, and a combination thereof; $0.9<\beta<1.1$; $0.7<x<1$; $0<y<0.3$; $0<z<0.3$; and $x+y+z=1$. In some variations of Formula (VIIb), $0.05<y<0.3$ and $0.05<z<0.3$.

In other variations, this disclosure is directed to particles (e.g., a powder) comprising a compound represented by Formula (VIIc):

$$Li_\beta Ni_x Mn_y Mg_z O_2 \qquad (VIIc)$$

where $0.9<\beta<1.1$; $0.7<x<1$; $0<y<0.3$; $0<z<0.3$; and $x+y+z=1$. In some variations of Formula (VIIc), $0.05<y<0.3$ and $0.05<z<0.3$.

In compounds of Formula (VIIc), a valence of Mg remains 2+ and a valence of Mn remains 4+. Again, without wishing to be held to a particular theory or mode of action, the valence of Mg remains 2+ to stabilize a layered crystal structure and improve electrochemical performance of the cathode active materials represented by Formula (VIIc). As compared to known cathode formulae, the amount of $Ni^{2+}$ can be reduced to achieve charge balance. Unlike $Ni^{2+}$, which can transition electronically to $Ni^{3+}$, $Mg^{2+}$ represents a stable divalent ion in the cathode active material. Thus, in order to maintain an average transition-metal valency of 3+, a presence of $Mg^{2+}$ in the cathode active material biases Ni away from $Ni^{2+}$ to $Ni^{3+}$. Such bias towards $Ni^{3+}$ is decreases the availability of $Ni^{2+}$ to occupy a $Li^+$ site, which decreases performance of the cathode active material.

In some variations, Ni is an active transition metal at a higher stoichiometric amount than in conventional materials. In further variations, the active transition metal of Ni is trivalent in the material (i.e., 3+). During an electrochemical charge/discharge process in a cell, the redox couple between $Ni^{3+}/Ni^{4+}$ influences a capacity of the cell.

The compounds of Formulae (VIIb) and (VIIc) as disclosed herein have properties that are surprisingly improved over properties of known compositions.

In some variations, this disclosure is directed to particles (e.g., a powder) comprising a compound represented by Formula (VIIIa):

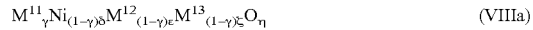

$$M^{11}{}_\gamma Ni_{(1-\gamma)\delta} M^{12}{}_{(1-\gamma)\varepsilon} M^{13}{}_{(1-\gamma)\zeta} O_\eta \qquad (VIIIa)$$

where $M^{11}$ is selected from Mn, Ti, Ru, Zr, and any combination thereof; $M^{12}$ is selected from Mn, Ti, Zr, Ge, Sn, Te, and any combination thereof; $M^{13}$ is selected from Mg, Be, Ca, Sr, Ba, Fe, Ni, Cu, Zn, and any combination thereof; $0 \leq \gamma \leq 0.3$; $0.7<\delta<1$; $0<\varepsilon<0.3$; $0<\zeta<0.3$; $\delta+\varepsilon+\zeta=1$; and $0.9 \leq \eta \leq 2.6$.

In some variations of Formula (VIIIa), $0.05<\varepsilon<0.3$ and $0.05<\zeta<0.3$. In some variations, $1.4 \leq \eta \leq 2.1$. In some variations, $1.5 \leq \eta \leq 2.0$. In some variations, $1.6 \leq \eta \leq 1.9$. In some variations, $0.9 \leq \eta \leq 1.1$. In some variations, $\eta=1$. In some variations, $1.4 \leq \eta \leq 1.6$. In some variations, $\eta=1.5$. In some variations, $1.9 \leq \eta \leq 2.1$. In some variations, $\eta=2$. In some variations, $2.4 \leq \eta \leq 2.6$. In some variations, $\eta=2.5$.

In some variations, a stabilizer component is added to an active component in the cathode active material. As such, the cathode active material includes a compound represented by Formula (VIIIb):

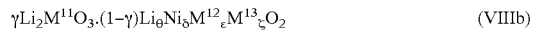

$$\gamma Li_2 M^{11}O_3.(1-\gamma)Li_\theta Ni_\delta M^{12}{}_\varepsilon M^{13}{}_\zeta O_2 \qquad (VIIIb)$$

In Formula (VIIIb), $Li_\theta Ni_\delta M^{12}{}_\varepsilon M^{13}{}_\zeta O_2$ serves as the active component and $Li_2 M^{11}O_3$ serves as the stabilizer component. The compound of Formula (VIIIb) corresponds to integrated or composite oxide material. A ratio of the components is governed by $\gamma$, which ranges according to $0 \leq \gamma \leq 0.3$. For the $Li_2 M^{11}O_3$ stabilizer component, $M^{11}$ is selected from Mn, Ti, Ru, Zr, and any combination thereof. For the $Li_\theta Ni_\delta M^{12}{}_\varepsilon M^{13}{}_\zeta O_2$ active component, $M^{12}$ is selected from Mn, Ti, Zr, Ge, Sn, Te, and any combination thereof; $M^{13}$ is selected from Mg, Be, Ca, Sr, Ba, Fe, Ni, Cu, Zn, and any combination thereof; $0.9<\theta<1.1$; $0.7<\delta<1$; $0<\varepsilon<0.3$; $0<\zeta<0.3$; and $\delta+\varepsilon+\zeta=1$. In some variations of Formula (VIIIb), $0.05<\varepsilon<0.3$ and $0.05<\zeta<0.3$.

In other variations, the disclosure is directed to a compound represented by Formula (VIa):

$$(v)[M^7O_2].(1-v)[Co_{1-\sigma}M^8{}_\sigma O_2] \qquad (VIa)$$

wherein $M^7$ is one or more elements with an average oxidation state of 4+(i.e., tetravalent); $M^8$ is one or more monovalent, divalent, trivalent, and tetravalent elements; $0.01 \leq v<1.00$, and $0.5 \leq$ and $0 \leq \sigma \leq 0.05$. In some variations, $M^7$ is selected from Mn, Ti, Zr, Ru, and a combination thereof. In some variations, $M^8$ is selected from B, Na, Mg, Ti, Ca, V, Cr, Mn, Fe, Co, Ni, Cu, Zn, Al, Sc, Y, Ga, Zr, Ru, Mo and a combination thereof. In some variations, $M^7$ is Mn. In some variations, $M^8$ is Al.

In some embodiments, 0.01≤v≤0.50. In some embodiments, 0.01≤v<0.50. In some embodiments, 0.01≤v<0.30. In some embodiments, 0.01≤v<0.10. In some embodiments, 0.01≤v<0.05. In some variations, 0≤σ≤0.05. In some variations, 0<σ≤0.05. In some variations, 0<σ≤0.03. In some variations, 0<σ≤0.02. In some variations, 0<σ≤0.01. In some variations, 0.01≤v<0.05 and 0<σ≤0.05.

In some variations, Al is at least 500 ppm. In some variations, Al is at least 750 ppm. In some variations, Al is at least 900 ppm. In some variations, Al is less than or equal to 2000 ppm. In some variations, Al is less than or equal to 1500 ppm. In some variations, Al is less than or equal to 1250 ppm. In some variations, Al is less than or equal to 1000 ppm. In some variations, Al is less than or equal to 900 ppm. In some variations, Al is less than or equal to 800 ppm. In some variations, Al is less than or equal to 700 ppm. In some variations, Al is less than or equal to 600 ppm. In some instances, when $M^8$ (e.g., Al) is expressed in ppm, in optional variations, the compound can be represented as $(v)[Li_2M^7O_3]\cdot(1-v)[Li_\alpha Co_w O_2]$ and the amount of $M^8$ can be represented as $M^8$ in at least a quantity in ppm, as otherwise described above. In some embodiments, 0.5≤w≤1. In some embodiments, 0.8≤w≤1. In some embodiments, 0.96≤w≤1. In some embodiments, 0.99≤w≤1. In some embodiments, w is 1. In other variations, this disclosure is directed to a compound represented by Formula (VIb):

$$(v)[Li_2M^7O_3]\cdot(1-v)[Li_\alpha Co_{1-\sigma}M^8{}_\sigma O_2] \quad \text{(VIb)}$$

wherein $M^7$ is one or more elements with an average oxidation state of 4+ (i.e., tetravalent); $M^8$ is one or more monovalent, divalent, trivalent, and tetravalent elements; 0.95≤α<0.99; 0.01≤v<1.00, and 0.5≤w≤1, and 0≤σ≤0.05. In some variations, $M^7$ is selected from Mn, Ti, Zr, Ru, and a combination thereof. In some variations, $M^8$ is selected from B, Na, Mg, Ti, Ca, V, Cr, Mn, Fe, Co, Ni, Cu, Zn, Al, Sc, Y, Ga, Zr, Ru, Mo and a combination thereof. In some variations, $M^7$ is Mn. In some variations, $M^8$ is Al.

In some embodiments, 0.01≤v≤0.50. In some embodiments, 0.01≤v<0.50. In some embodiments, 0.01≤v<0.30. In some embodiments, 0.01≤v<0.10. In some embodiments, 0.01≤v<0.05. In some variations, 0≤σ≤0.05. In some variations, 0<σ≤0.05. In some variations, 0<σ≤0.03. In some variations, 0<σ≤0.02. In some variations, 0<σ≤0.01. In some variations, 0.95≤α<0.99, 0.01≤v<0.05, 0.96≤w<1, and 0<σ≤0.05.

In some variations, $M^8$ (e.g., Al) is at least 500 ppm. In some variations, $M^8$ (e.g., Al) is at least 750 ppm. In some variations, $M^8$ (e.g., Al) is at least 900 ppm. In some variations, $M^8$ (e.g., Al) is less than or equal to 2000 ppm. In some variations, $M^8$ (e.g., Al) is less than or equal to 1500 ppm. In some variations, $M^8$ (e.g., Al) is less than or equal to 1250 ppm. In some variations, $M^8$ (e.g., Al) is less than or equal to 1000 ppm. In some variations, $M^8$ (e.g., Al) is less than or equal to 900 ppm. In some variations, $M^8$ (e.g., Al) is less than or equal to 800 ppm. In some variations, $M^8$ (e.g., Al) is less than or equal to 700 ppm. In some variations, $M^8$ (e.g., Al) is less than or equal to 600 ppm. In some instances, when $M^8$ (e.g., Al) is expressed in ppm, the compound can be represented as $(v)[Li_2M^7O_3]\cdot(1-v)[Li_\alpha Co_w O_2]$ and the amount of $M^8$ can be represented as $M^8$ in at least a quantity in ppm, as otherwise described above. In some variations, 0.5≤w≤1. In some variations, 0.8≤w≤1. In some variations, 0.96≤w≤1. In some variations, 0.99≤w≤1. In some variations, w is 1.

Figure 1B:
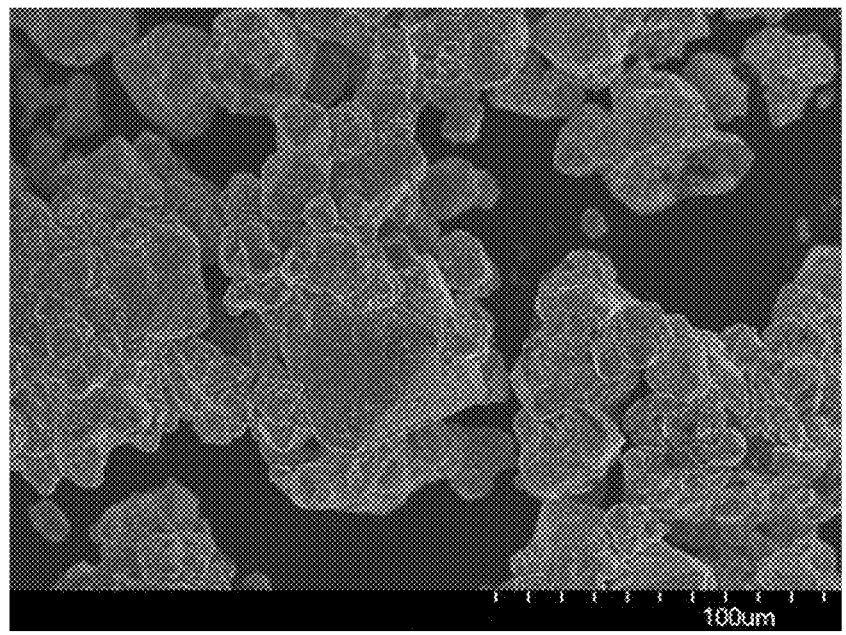
FIG. 1B is a scanning electron micrograph of particles of the lithiated mixed-metal oxide $Li_{1.06}Ni_{1/3}Mn_{1/3}Co_{1/3}O_2$ prepared by lithiating the particles of FIG. 1A, according to some illustrative embodiments.
Figure 1C:
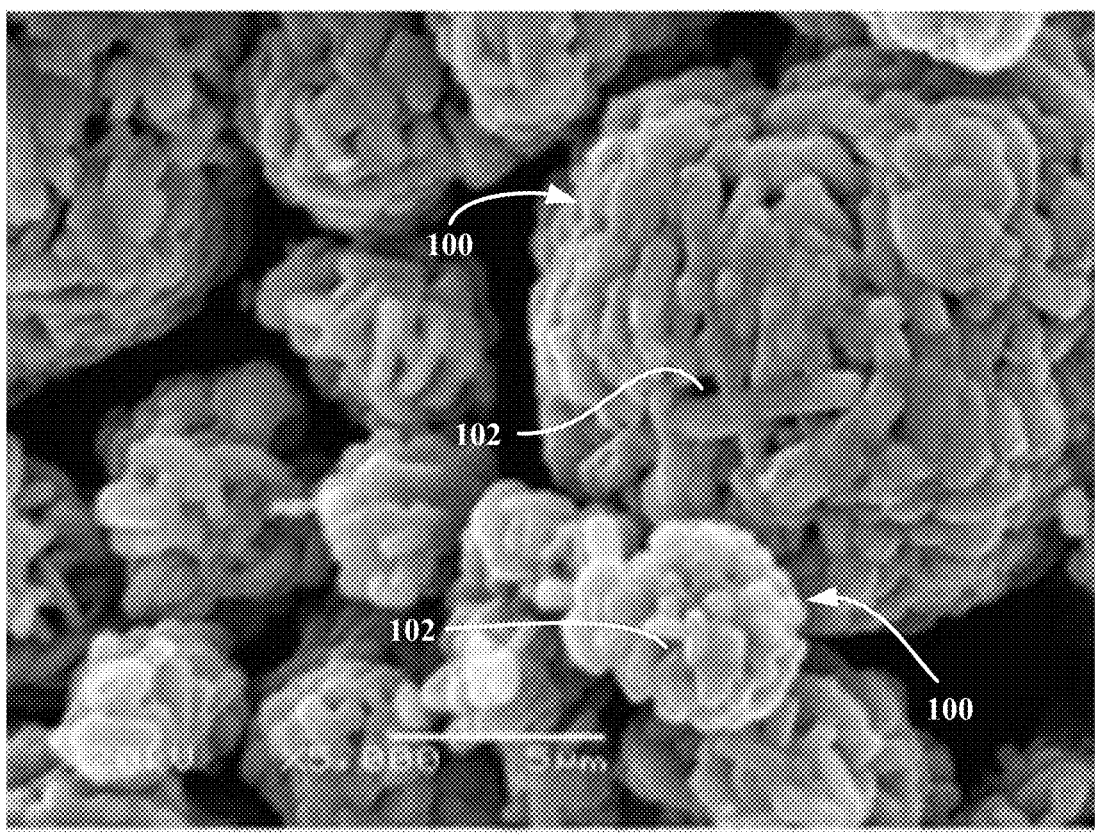
FIG. 1C is a scanning electron micrograph of a conventional powder having spherical aggregates formed of $LiNi_{1/3}Mn_{1/3}Co_{1/3}O_2$.

Particles of the mixed-metal oxides and the lithiated mixed-metal oxides exhibit morphologies substantially free of voids and pores. FIG. 1A presents a scanning electron micrograph of particles of $Ni_{1/3}Mn_{1/3}Co_{1/3}O_\beta$ (i.e., a mixed-metal oxide) prepared by methods disclosed herein, according to some illustrative embodiments (i.e., see also Example 3). The particles, which exhibit a void- and pore-free morphology, correspond to primary particles and include virtually no secondary particles. Crystalline facets are visible on many of the particles, indicating a presence of crystallites. FIG. 1B presents a scanning electron micrograph of particles of $Li_{1.06}Ni_{1/3}Mn_{1/3}Co_{1/3}O_2$ prepared by lithiating the particles of FIG. 1A, according to some illustrative embodiments (i.e., see also Example 6). These particles, which also correspond to primary particles, retain the void- and pore-free morphology of the particles of FIG. 1A. Secondary particles are absent from the particles of $Li_{1.06}Ni_{1/3}Mn_{1/3}Co_{1/3}O_2$. Octahedral crystal habits are visible on many of the particles, indicating a presence of crystallites. In contrast, FIG. 1C presents a scanning electron micrograph of a conventional powder having spherical aggregates 100 formed of $LiNi_{1/3}Mn_{1/3}Co_{1/3}O_2$. The spherical aggregates 100, which are present almost exclusively, correspond to secondary particles and were prepared via lithiation of hydroxide precursors (i.e., via conventional manufacturing). Voids and pores 102 are clearly present in the spherical aggregates 100.

The particle morphologies of the mixed-metal oxides and the lithiated mixed-metal oxides allow high particulate densities approaching (or equaling) those associated with single crystals. In some variations, particles of the mixed-metal oxides and the lithiated mixed-metal oxides may include, in whole or in part, crystallites having morphologies that reflect a symmetry of an underlying crystalline lattice. These crystallites correspond to single-crystal particles displaying crystal habits (e.g., crystal facets, crystal edges, etc.). Non-limiting examples of such morphologies include cubic crystal habits, tetrahedral crystal habits, octahedral crystal habits, rhombic crystal habits, hexagonal crystal habits, dodecahedral crystal habits, and so forth. Other crystal habits are possible for the crystallites, including those in which one or more crystallites grows out of another (e.g., twinning). Particle morphologies for the mixed-metal oxides and lithiated mixed-metal oxides will be discussed additionally in relation to Examples 1-8.

The high particulate densities of the mixed-metal oxides and the lithiated mixed-metal oxides may be referenced relative to an ideal crystalline density. As used herein, the term "particulate density" refers to a density based on a volume conformally enveloping an outer periphery of a particle. This enveloping volume includes a mass of the particle as well as an absence of mass, i.e., voids and pores (if present). Techniques to measure particulate densities (e.g., pycnometry, mercury porosimetry, hydrostatic weighing, etc.) are known to those skilled in the art and will not be discussed further. The term "ideal crystalline density", as used herein, refers to a density determined by dividing a mass associated with a crystalline lattice cell with a volume of the crystalline lattice cell. It will be appreciated that the crystalline lattice cell may vary in dimensions and atomic content with composition. Without being limited by theory, Equation (1) presents a mathematical relationship between parameters useful for determining the ideal crystalline density (ρ):

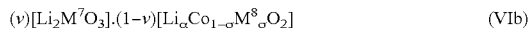

$$\rho = \frac{[M \cdot Z / N_A]}{\left[abc\sqrt{1 - \cos^2\alpha - \cos^2\beta - \cos^2\gamma - 2\cos\alpha\cos\beta\cos\gamma}\right]} \quad (1)$$

The numerator and the denominator of Equation (1) correspond to, respectively, the mass and the volume of the crystalline lattice cell. The mass may be calculated by multiplying a molecular mass (III) of a compound by a number of formula units of the compound in the crystalline lattice cell (Z). The resulting product is then divided by Avogadro's constant (i.e., $N_A=6.02212 \times 10^{23}$ $mol^{-1}$). The volume may be calculated using lattice constants of the crystalline lattice cell (i.e., a, b, c) and corresponding angles therebetween (i.e., $\alpha$, $\beta$, $\gamma$). Equation (1) and its associated parameters are understood by those skilled in the art and will not be discussed further here.

The molecular mass (M) of the compound may be measured by those skilled in the art using techniques of chemical analysis, such as inductively coupled plasma optical emission spectrometry (ICP-OES), iodometric titration, and so forth. Those skilled in the art may also determine the number of formula units, lattice constants, and lattice angles of the compound using techniques of crystal structure analysis (e.g., X-ray diffraction, neutron diffraction, electron diffraction, etc.). Characterization of the crystalline lattice cell (i.e., the mass and volume thereof) may utilize or reference a bulk single crystal or multiple single-crystal particles (e.g., a powder of crystallites).

In some variations, each of the particles of the mixed-metal oxides has a density greater than or equal to 90% of an ideal crystalline density of the particle. In some variations, each of the particles of the mixed-metal oxides has a density greater than or equal to 92% of an ideal crystalline density of the particle. In some variations, each of the particles of the mixed-metal oxides has a density greater than or equal to 94% of an ideal crystalline density of the particle. In some variations, each of the particles of the mixed-metal oxides has a density greater than or equal to 96% of an ideal crystalline density of the particle. In some variations, each of the particles of the mixed-metal oxides has a density greater than or equal to 98% of an ideal crystalline density of the particle.

In some variations, each of the particles of the lithiated mixed-metal oxides has a density greater than or equal to 90% of an ideal crystalline density of the particle. In some variations, each of the particles of the lithiated mixed-metal oxides has a density greater than or equal to 92% of an ideal crystalline density of the particle. In some variations, each of the particles of the lithiated mixed-metal oxides has a density greater than or equal to 94% of an ideal crystalline density of the particle. In some variations, each of the particles of the lithiated mixed-metal oxides has a density greater than or equal to 96% of an ideal crystalline density of the particle. In some variations, each of the particles of the lithiated mixed-metal oxides has a density greater than or equal to 98% of an ideal crystalline density of the particle.

When referred to a plurality of or population of lithiated or unlithiated particles, it will be appreciated that the density can be referred to as an average density. In some variations, the particles have an average density greater than or equal to 90% of an ideal crystalline density of the particles. In some variations, the particles have an average density greater than or equal to 92% of an ideal crystalline density of the particles. In some variations, the particles have an average density greater than or equal to 94% of an ideal crystalline density of the particles. In some variations, the particles have an average density greater than or equal to 96% of an ideal crystalline density of the particles. In some variations, the particles have an average density greater than or equal to 98% of an ideal crystalline density of the particles.

In some variations, the particles of the mixed-metal oxides include crystallites. The crystallites may be greater in number than 20% of the particles. In some instances, the crystallites are greater in number than 40% of the particles. In some instances, the crystallites are greater in number than 60% of the particles. In some instances, the crystallites are greater in number than 80% of the particles. In some instances, the crystallites are greater in number than 90% of the particles.

In some variations, the particles of the lithiated mixed-metal oxides include crystallites. The crystallites may be greater in number than 20% of the particles. In some instances, the crystallites are greater in number than 40% of the particles. In some instances, the crystallites are greater in number than 60% of the particles. In some instances, the crystallites are greater in number than 80% of the particles. In some instances, the crystallites are greater in number than 90% of the particles.

Particle morphologies of the mixed-metal oxides and the lithiated mixed-metal oxides also allow for powders having high proportions of primary particles (i.e., greater than 50% in number). Such high proportions limit a presence of secondary particles, which occur in low proportions (i.e., less than 50% in number). As used herein, the term "secondary particles" refers to aggregates of primary particles chemically-bonded or sintered together. These secondary particles may exhibit voids (i.e., cavities internal to a particle) or pores (i.e., cavities connected to an exterior of the particle). Powders of the lithiated mixed-metal oxides, which are prepared from powders of the mixed-metal oxides, are tolerant of calendaring processes due to their high proportions of primary particles. Calendaring processes utilize high pressures (e.g., >100 MPa) to form layers of cathode active material for cathodes of a battery cell. In contrast to secondary particles, primary particles are highly resistant to fracture under these pressures. Such resistance is poor in conventional powders of the lithiated mixed-metal oxides, which contain high proportions of secondary particles.

In some variations, the particles of the mixed-metal oxide include primary particles. The primary particles may be greater in number than 50% of the particles. In some instances, the primary particles are greater in number than 60% of the particles. In some instances, the primary particles are greater in number than 70% of the particles. In some instances, the primary particles are greater in number than 80% of the particles. In some instances, the primary particles are greater in number than 90% of the particles. In some instances, the primary particles are greater in number that 95% of the particles.

In some variations, the particles of the lithiated mixed-metal oxide include primary particles. The primary particles may be greater in number than 50% of the particles. In some instances, the primary particles are greater in number than 60% of the particles. In some instances, the primary particles are greater in number than 70% of the particles. In some instances, the primary particles are greater in number than 80% of the particles. In some instances, the primary particles are greater in number than 90% of the particles. In some instances, the primary particles are greater in number that 95% of the particles.

The primary particles—whether formed of mixed-metal oxide or lithiated mixed-metal oxide—may have a mean particle size less than 100 μm. These mean particle sizes may correspond to particles having densities greater than or equal to 90% of an ideal crystalline density of the particle. In some variations, the primary particles of the mixed-metal oxides have a mean particle size from 1 to 50 µm. The primary particles may include crystallites in whole or in part. In other variations, the primary particles of the mixed-metal oxides have a mean particle size between 10 and 20 µm. Theses primary particles may also include crystallites in whole or in part. In some variations, the primary particles of the lithiated mixed-metal oxides have a mean particle size from 1 to 50 µm. The primary particles may include crystallites in whole or in part. In other variations, the primary particles of the lithiated mixed-metal oxides have a mean particle size between 10 and 20 µm. These primary particles may also include crystallites in whole or in part.

It will be understood that the primary particles may include any combination of mean particle sizes. Such combinations may allow the primary particles to form powders of high packing efficiency. In some variations, the primary particles of the mixed-metal oxides include a first portion having a mean particle size from 1 to 50 µm. In some of these variations, the primary particles further include a second portion having a mean particle size between 1 and 5 µm. The primary particles may also include a third portion having a mean particle size between 10 and 20 µm. In some variations, the primary particles of the lithiated mixed-metal oxides include a first portion having a mean particle size from 1 to 50 µm. In some of these variations, the primary particles include a second portion having a mean particle size between 1 and 5 µm. The primary particles may also include a third portion having a mean particle size between 10 and 20 µm.

The lithiated mixed-metal oxide compounds of Formula (II) may be synthesized using the mixed-metal oxides of Formula (I) as precursors. According to some illustrative embodiments, a method for manufacturing the mixed-metal oxides includes preparing a solution of metal chlorides selected from the group consisting of Ni, Mn, Co, and Me. Me is one or more elements of B, Na, Mg, Al, Si, K, Ca, Sc, Ti, V, Cr, Fe, Cu, Zn, Ga, Ge, Zr, Nb, Mo, Ru, Ag, and In. The solution may be an aqueous solution, and during preparation, the metal chlorides may be dissolved in any sequence or concentration therein. The aqueous solution may be agitated (e.g., stirred) to accelerate dissolution and mixing, which may also involve heating.

The method also includes drying the solution (e.g., via evaporation) to form a mixed-metal precursor. Drying the solution may involve heating the solution according to a predetermined process schedule, which represents any combination of temperatures and times (e.g., stir under a constant temperature of 70° C. until dry). The mixed-metal precursor so-dried may incorporate any combination of oxygen (O), chloride (Cl), or hydroxide (OH) ligands. For example, and without limitation, the mixed-metal precursor may be a mixed-metal chloride compound, a mixed-metal oxide compound, a mixed-metal hydroxide compound, a mixed-metal oxychloride compound, a mixed-metal hydroxychloride compound, or a mixed-metal oxohydroxychloride compound. Such compounds may also include water ($H_2O$) ligands (i.e., be hydrated compounds).

The method additionally includes heating the mixed-metal precursor to form the mixed-metal oxide. In these embodiments, the mixed-metal precursor may first be heated at an intermediate temperature (e.g., 200° C.) before subsequent heating at a first elevated temperature (e.g., 700° C.). Between heatings, the mixed-metal precursor may be cooled and ground to form a powder of desired mean particle size. The first elevated temperature may be selected by those skilled in the art to ensure complete conversion of the mixed-metal precursor into the mixed-metal oxide.

In some embodiments, the method further includes reacting the mixed-metal oxide with a lithium precursor at a second, elevated temperature (e.g., 900° C.) to form a lithiated mixed-metal oxide. Non-limiting examples of the lithium precursor include lithium hydroxide, lithium carbonate, lithium oxalate, lithium nitrate, lithium chloride, lithium acetate, and lithium oxide. Other lithium precursors are possible. The second, elevated temperature may be higher than the first, elevated temperature. In some instances, an environment for reacting the mixed-metal oxide with the lithium precursor includes air. The second, elevated temperature and the environment may be selected by those skilled in the art to ensure complete lithiation of the mixed-metal oxide into the lithiated mixed-metal oxide. The lithiated mixed-metal oxide may be subsequently processed to produce a powder having a desired mean particle size (e.g., ground in a mortar and pestle, milling, crushing, sieving, etc.).

It will be appreciated that, during lithiation, the dense morphologies associated with the mixed-metal oxide are carried over to the lithiated mixed-metal oxide. Lithium from the lithium precursor reacts with and diffuses into particles of the mixed-metal oxide, but preserves a void- and pore-free structure of the latter oxide. Such preservation may also include preserving crystal habits associated with crystallites, if present. This aspect is not found in conventional manufacturing of cathode active materials. In conventional methods, precursors having high proportions of secondary particles are reacted to form lithiated products, which in turn, also have high proportions of secondary particles. Such lithiated secondary particles retain the voids and pores of their precursors.

Figure 2:
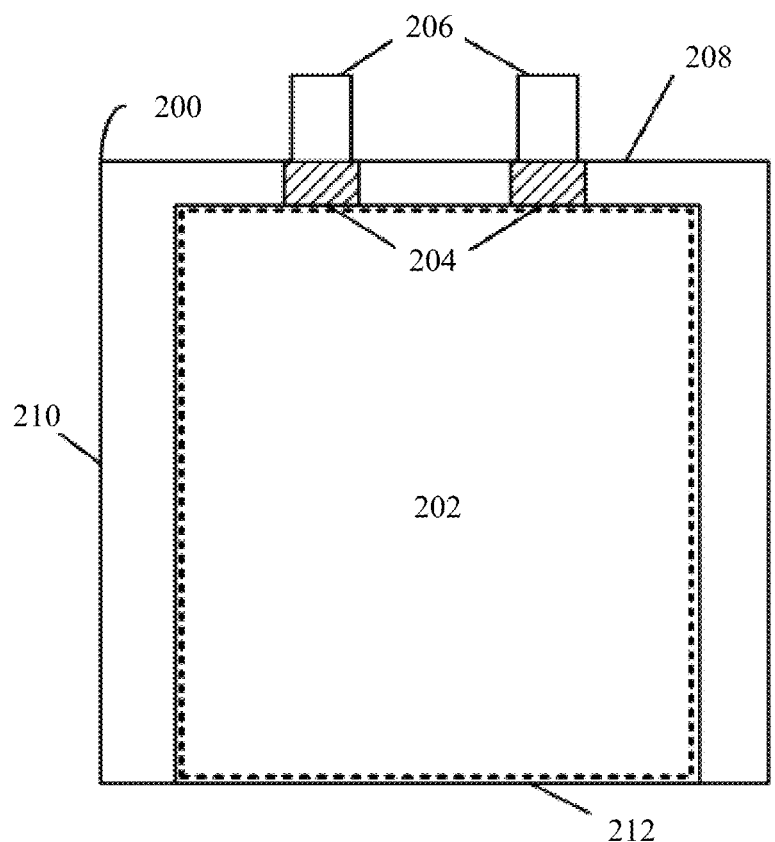
FIG. 2 is a top-down view of a battery cell, according to some illustrative embodiments.

The lithiated mixed-metal oxides described herein can be used as cathode active materials in conjunction with any battery cells known in the art. Now referring to FIG. 2, a top-down view is presented of a battery cell 200, according to some illustrative embodiments. The battery cell 200 may correspond to a lithium-ion or lithium-polymer battery cell. The battery cell 200 includes a stack 202 containing a number of layers that include a cathode with a cathode active coating, a separator, and an anode with an anode active coating. More specifically, the stack 202 may include one strip of cathode active material (e.g., aluminum foil coated with a lithium compound) and one strip of anode active material (e.g., copper foil coated with carbon). The stack 202 also includes one strip of separator material (e.g., ion-conducting polymer electrolyte) disposed between the one strip of cathode active material and the one strip of anode active material. The cathode, anode, and separator layers may be left flat in a planar configuration, or may be wrapped into a wound configuration (e.g., a "jelly roll").

Battery cells can be enclosed in a flexible pouch. Returning to FIG. 2, during assembly of the battery cell 200, the stack 202 is enclosed in a flexible pouch. The stack 202 may be in a planar or wound configuration, although other configurations are possible. The flexible pouch is formed by folding a flexible sheet along a fold line 212. For example, the flexible sheet may be made of aluminum with a polymer film, such as polypropylene. After the flexible sheet is folded, the flexible sheet can be sealed, e.g., by applying heat along a side seal 210 and along a terrace seal 208. The flexible pouch may be less than 120 microns thick to improve the packaging efficiency of the battery cell 200, the density of battery cell 200, or both.

The stack 202 also includes a set of conductive tabs 206 coupled to the cathode and the anode. The conductive tabs 206 may extend through seals in the pouch (e.g., formed using sealing tape 204) to provide terminals for the battery cell 200. The conductive tabs 206 may then be used to electrically couple the battery cell 200 with one or more other battery cells to form a battery pack. It will be recognized that any other manner of providing terminals for battery cells can be used in conjunction with this disclosure.

Batteries can be combined in a battery pack in any configuration. For example, the battery pack may be formed by coupling the battery cells in a series, parallel, or a series-and-parallel configuration. Such coupled cells may be enclosed in a hard case to complete the battery pack, or may be embedded within an enclosure of a portable electronic device, such as a laptop computer, tablet computer, mobile phone, personal digital assistant (PDA), digital camera, and/or portable media player.

Figure 3:
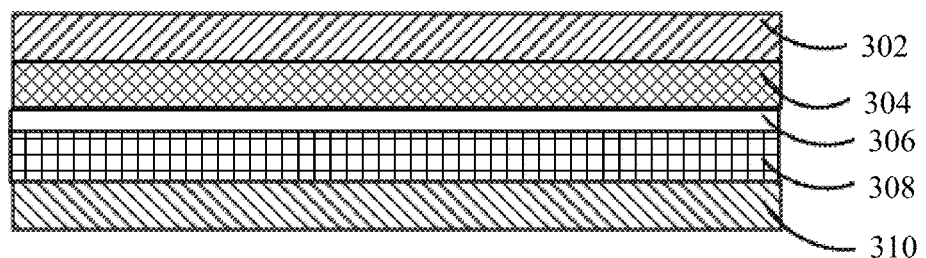
FIG. 3 is a side view of a set of layers for a battery cell, according to some illustrative embodiments.

FIG. 3 presents a side view of a set of layers for a battery cell (e.g., the battery cell 200 of FIG. 2), according to some illustrative embodiments. The set of layers may include a cathode current collector 302, an active coating 304, a separator 306, an anode active coating 308, and an anode current collector 310. The cathode and anode current collectors can be held together by a binder. The cathode current collector 302 and the cathode active coating 304 may form a cathode for the battery cell, and the anode current collector 310 and the anode active coating 308 may form an anode for the battery cell. To create the battery cell, the set of layers may be stacked in a planar configuration, or stacked and then wound into a wound configuration. It will be appreciated that the layers may be stacked and/or used to form other types of battery cell structures, such as bi-cell structures. All such battery cell structures are known in the art.

As mentioned above, the cathode current collector 302 may be aluminum foil, the cathode active coating 304 may be a lithium compound, the anode current collector 310 may be copper foil, the anode active coating 308 may be carbon, and the separator 306 may include a conducting polymer electrolyte.

EXAMPLES

Many examples of methods for manufacturing the mixed-metal oxides and the lithiated mixed-metal oxides are within the scope of this disclosure, some of which are detailed below. The examples are intended for illustration purposes only, and are not intended as limiting.

Example 1—$(Mn_{0.04}Co_{0.96})_3O_4$ 14.57 g of $CoCl_2.6H_2O$ and 0.5 g of $MnCl_2.4H_2O$ in 20 mL of were dissolved deionized water. The resulting solution was stirred on a hotplate to dry at 70° C., leaving a Co—Mn precursor. Heating the Co—Mn precursor at 200° C. for 5 hours yielded an anhydrous Co—Mn precursor, which was subsequently ground in a mortar and pestle. The anhydrous Co—Mn precursor was subsequently fired in air at 10° C./min to 700° C. and then held for 10 hours (i.e., at 700° C.). Cooling to ambient temperature yielded a mixed-metal oxide. Chemical analysis by ICP-OES indicated an Mn:Co ratio of 0.04:0.96, which is consistent with a molar ratio of chloride salts. By virtue of a pure spinel structure (see below), an atomic oxygen content (i.e., β) was determined to be about 1.33, which on an integer basis, corresponds to about 4.

Figure 4A:
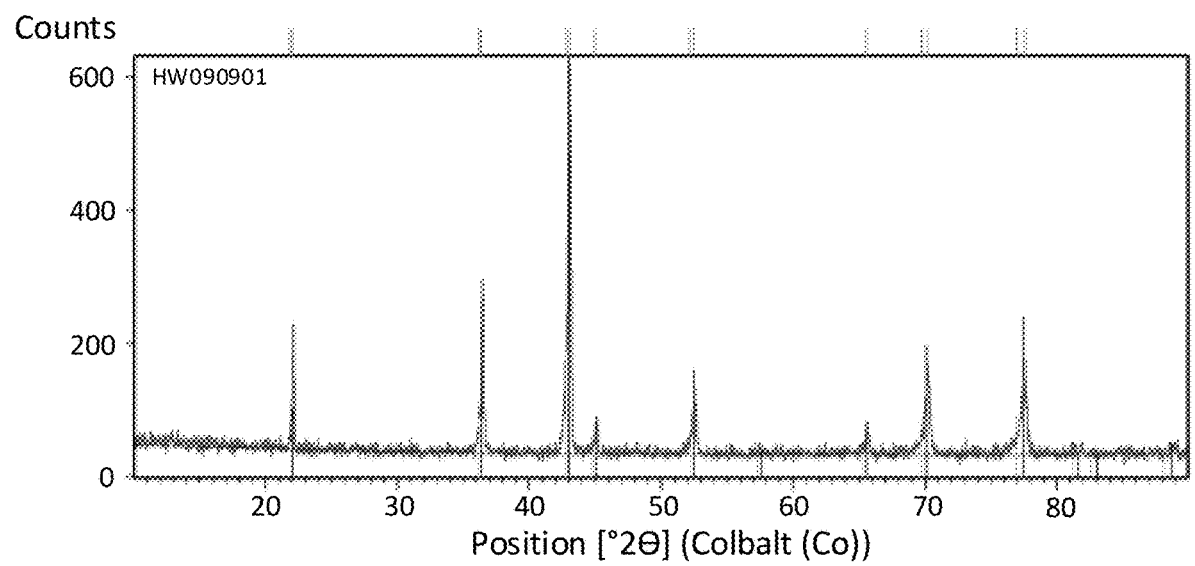
FIG. 4A is a powder X-ray diffraction pattern of the mixed-metal oxide $(Mn_{0.04}Co_{0.96})_3O_4$, according to some illustrative embodiments.
Figure 4B:
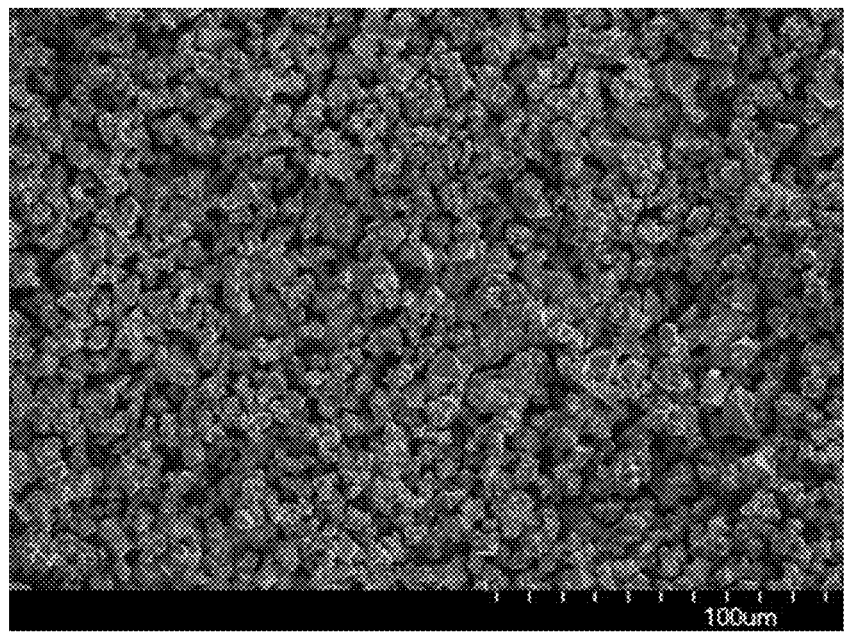
FIG. 4B is a scanning electron micrograph of particles of the mixed-metal oxide of FIG. 4A at 500× magnification.
Figure 4C:
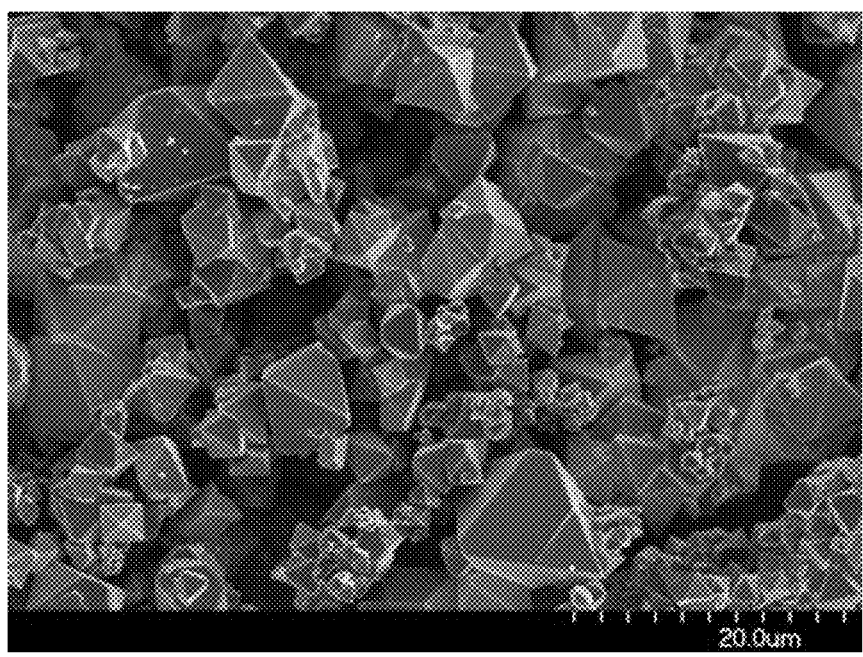
FIG. 4C is a scanning electron micrograph of particles of the mixed-metal oxide of FIG. 4A at 2000× magnification.
Figure 4D:
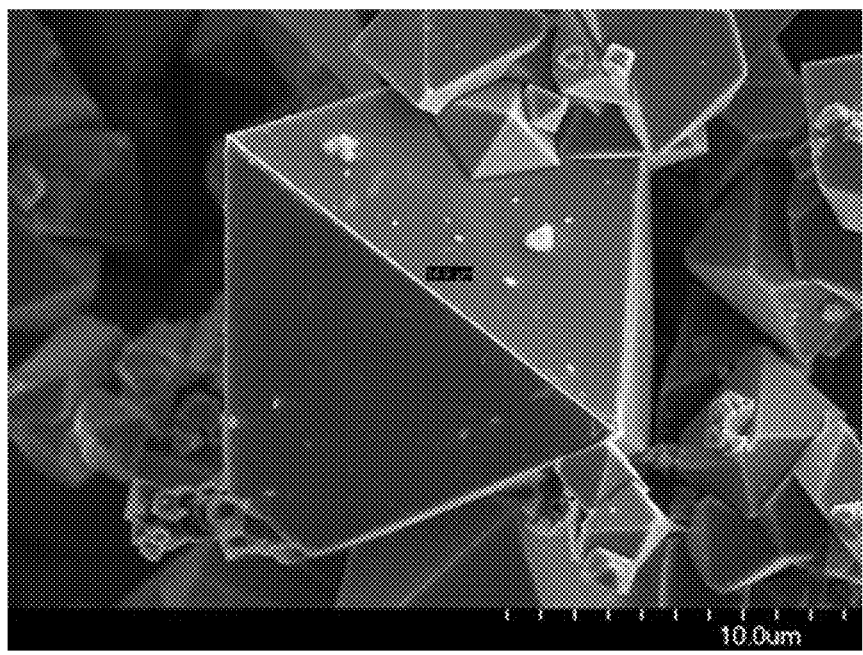
FIG. 4D is a scanning electron micrograph of particles of the mixed-metal oxide of FIG. 4A at 5000× magnification.

FIG. 4A presents a powder X-ray diffraction pattern of the mixed-metal oxide, i.e., $(Mn_{0.04}Co_{0.96})_3O_4$, according to some illustrative embodiments. The powder X-ray diffraction pattern corresponds to particles having a spinel crystalline structure. No other crystalline phases are present. FIGS. 4B-4D present scanning electron micrographs of particles of the mixed-metal oxide of FIG. 4A, each at progressively higher magnification (i.e., 500×, 2000×, and 5000× magnification, respectively). The micrographs show particles having octahedral faces and edges, with virtually no voids or pores. The octahedral faces may correspond (111) planes of the spinel crystalline lattice. Such morphology corresponds to a crystal habit of octahedral crystallites. Some crystallites have nucleated and grown out of surfaces of other crystallites. However, it will be appreciated that no secondary particles are present: Aggregates of chemically- or thermally-fused crystallites are absent the micrographs shown in FIGS. 4B-4D. Moreover, the particles display a consistent, uniform morphology. A mean particle size, i.e., a D50 particle size, was measured at 18.3 μm. D10 and D90 particle sizes were determined to be, respectively, 9.2 μm and 58.7 μm. A tap density of the mixed-metal oxide was measured at 2.02 g/cm³.

Figure 5A:
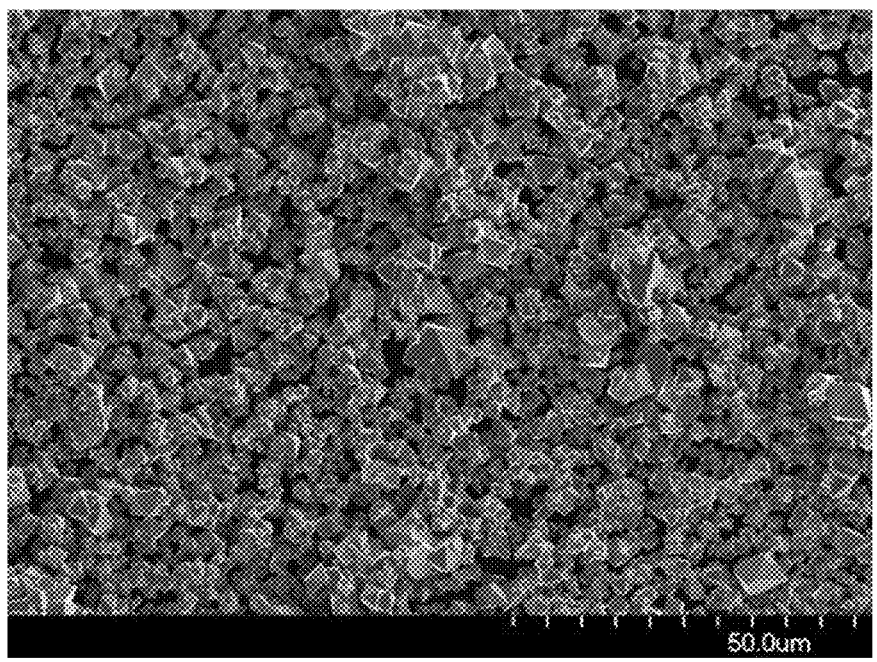
FIG. 5A is a scanning electron micrograph at 1000× magnification of particles of the mixed-metal oxide $(Mn_{0.20}Co_{0.80})_3O_4$, according to some illustrative embodiments.
Figure 5B:
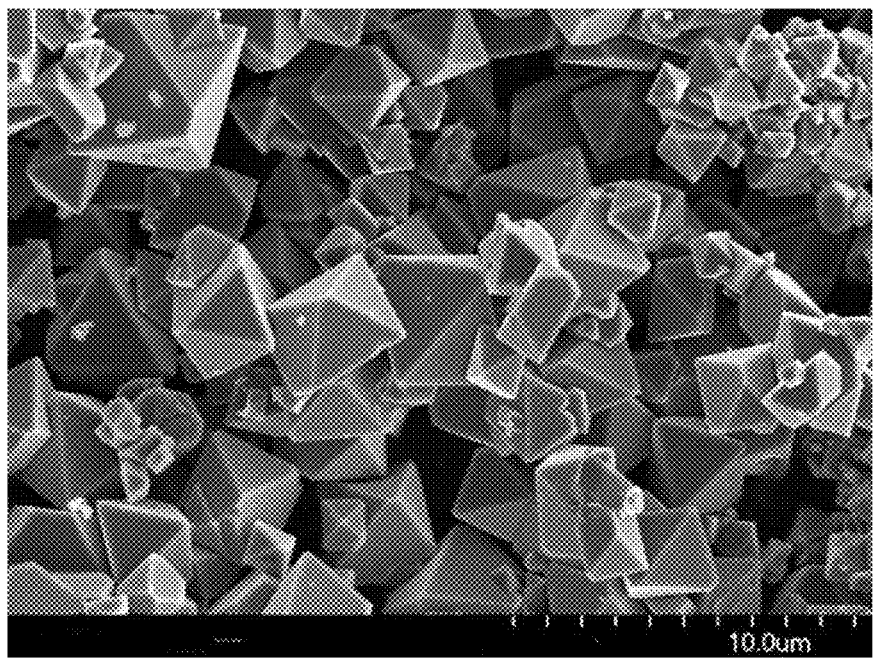
FIG. 5B is a scanning electron micrograph at 5000× magnification of the particles of FIG. 5B.

Example 2—$(Mn_{0.20}Co_{0.80})_3O_4$ 18.986 g of $CoCl_2.6H_2O$ and 3.9582 g of $MnCl_2.4H_2O$ were dissolved in 20 mL of deionized water. Subsequent processing was similar to Example 1. FIGS. 5A-5B present scanning electron micrographs of particles of the mixed-metal oxide $(Mn_{0.20}Co_{0.80})_3O_4$ each at progressively higher magnification (i.e., 1000× and 5000× magnification, respectively), according to some illustrative embodiments. The scanning electron micrographs reveal particles of virtually all octahedral crystallites. No pores or voids are observed therein.

Example 3—$Ni_{1/3}Mn_{1/3}Co_{1/3}O_\beta$ 7.923 g $NiCl_2.6H_2O$, 6.597 g of $CoCl_2.6H_2O$, and 7.91 g of $MnCl_2.4H_2O$ were dissolved in 20 mL of deionized water. Subsequent processing was similar to Example 1. Chemical analysis by ICP-OES indicated an Ni:Mn:Co ratio of 0.336:0.329:0.335, which is consistent with a molar ratio of chloride salts. FIG. 1A presents a scanning electron micrograph of particles of the mixed-metal oxide of $Ni_{1/3}Mn_{1/3}Co_{1/3}O_\beta$, according to some illustrative embodiments. (FIG. 1A is also discussed above.) The particles include dense, void- and pore-free primary particles with virtually no secondary particles. Many particles display crystalline facets, indicating a presence of crystallites.

Figure 6:
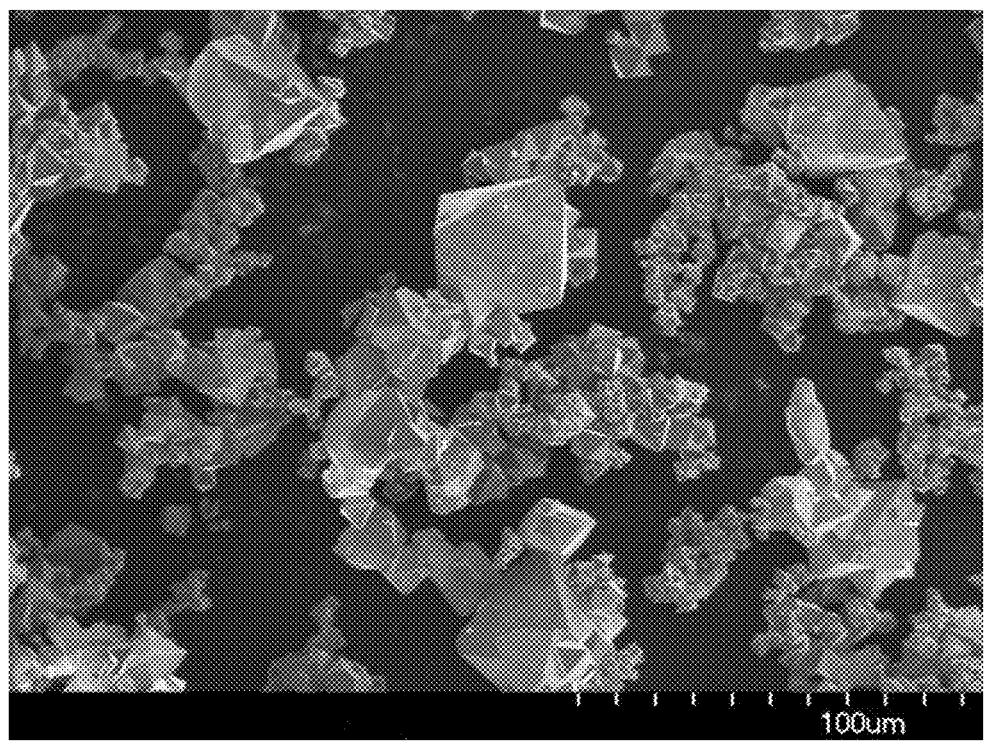
FIG. 6 is a scanning electron micrograph of particles of the mixed-metal oxide $Ni_{0.8}Mn_{0.1}Co_{0.1}O_\beta$, according to some illustrative embodiments.

Example 4—$Ni_{0.8}Mn_{0.1}Co_{0.1}O_\beta$ 19.0152 g $NiCl_2.6H_2O$, 1.9791 g of $CoCl_2.6H_2O$, and 2.3733 g of $MnCl_2.4H_2O$ were dissolved in 20 mL of deionized water. Chemical analysis by ICP-OES indicated an Ni:Mn:Co ratio of 0.749:0.130:0.121, which is consistent with a molar ratio of chloride salts and close to 0.8:0.1:0.1. Subsequent processing was similar to Example 1. FIG. 6 presents a scanning electron micrograph of particles of a mixed-metal oxide (i.e., $Ni_{0.8}Mn_{0.1}Co_{0.1}O_\beta$) at 500× magnification. The micrograph shows particles having octahedral faces and edges, with virtually no voids or pores. Such morphology corresponds to a crystal habit of octahedral crystallites. Some crystallites have nucleated and grown out of surfaces of other crystallites. However, it will be appreciated that no secondary particles are present: Aggregates of chemically- or thermally-fused crystallites are absent from the particles.

Example 5—$Li_{1.04}Mn_{0.04}Co_{0.96}O_2$

Figure 7A:
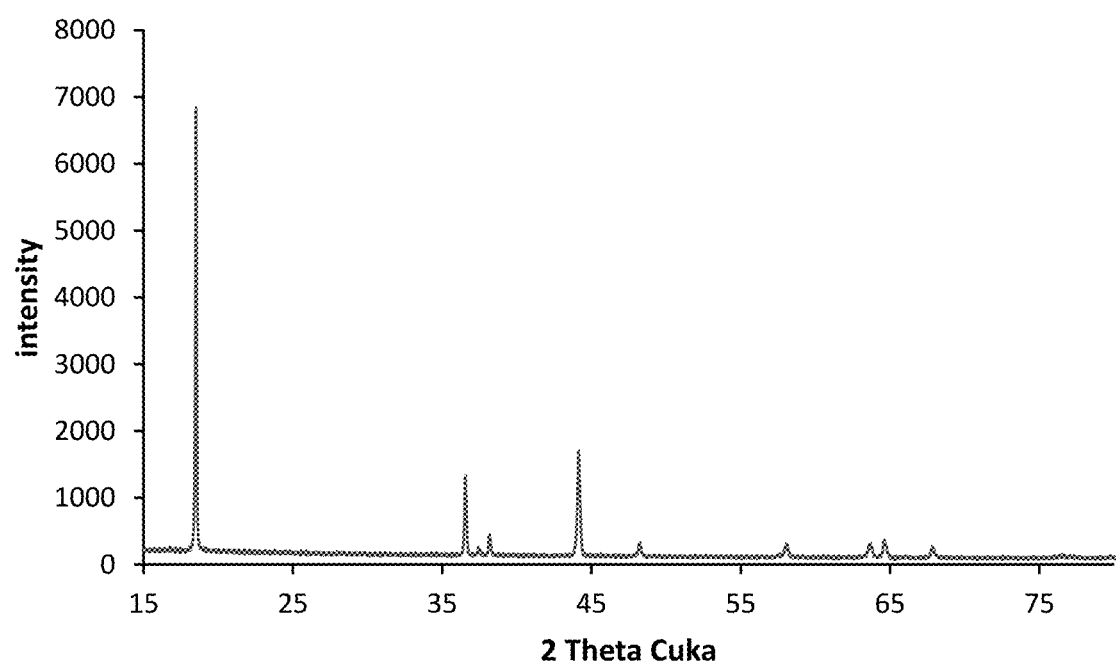
FIG. 7A is a powder X-ray diffraction pattern of the lithiated mixed-metal oxide $Li_{1.04}Mn_{0.04}Co_{0.96}O_2$ according to some illustrative embodiments.

A lithiated mixed-metal oxide compound of $Li_{1.04}Mn_{0.04}Co_{0.96}O_2$ was prepared by blending the mixed-metal oxide of Example 1 with $Li_2Co_3$ in a 1:1.04 molar ratio (i.e., [Mn,Co]:[Li]=1:1.04). The blend was fired in air at 900° C. for 16 hours. Chemical analysis by ICP-OES indicated an [Li]/[Mn,Co] quotient of 1.044, which is consistent with the molar ratio of lithium carbonate and the mixed-metal oxide. FIG. 7A presents a powder X-ray diffraction pattern of the lithiated mixed-metal oxide. The powder X-ray diffraction pattern reveals a layered, rhombohedral structure (i.e., space group $R\overline{3}m$) with no impurity phases (i.e., single phase). Based on this crystal structure, an atomic oxygen content (i.e., β) was determined to be 2. The phase-pure nature of the X-ray diffraction pattern confirms complete conversion of the spinel-structured, mixed-metal oxide (i.e., $Mn_{0.04}Co_{0.96}O_3$) into its rhombohedral-structured, lithiated derivative (i.e., $Li_{1.04}Mn_{0.04}Co_{0.96}O_2$). Lattice parameters of the lithiated mixed-metal oxide, using an equivalent hexagonal lattice cell (i.e., Z=3), were measured to be a, b=2.8112 Å and c=14.0711 Å (i.e., α, β=90°, γ=120°). Such values correspond to an ideal crystalline density of 5.069 $g/cm^3$.

Figure 7B:
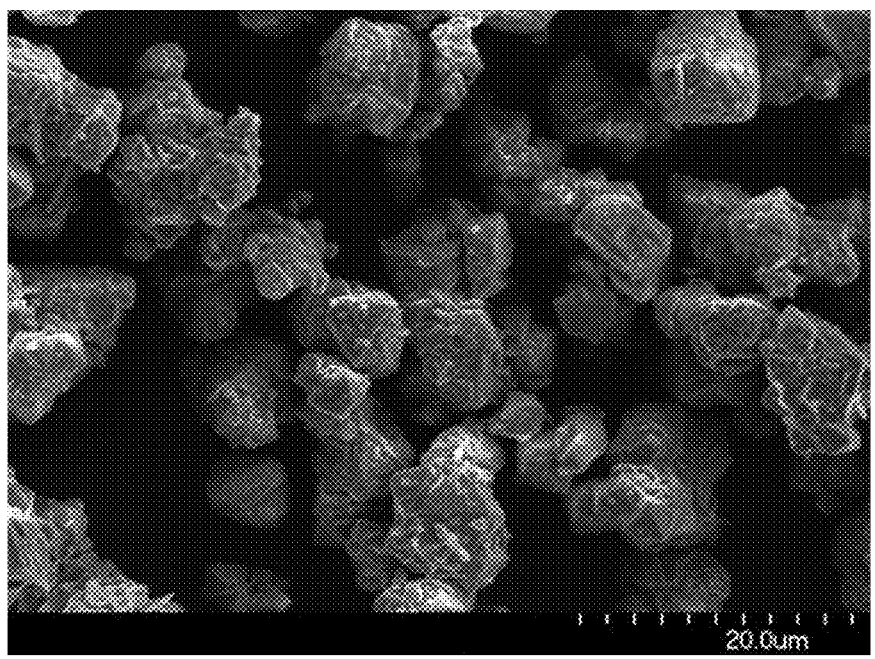
FIG. 7B is a scanning electron micrograph of particles of the lithiated mixed-metal oxide of FIG. 7A at 2000× magnification.
Figure 7C:
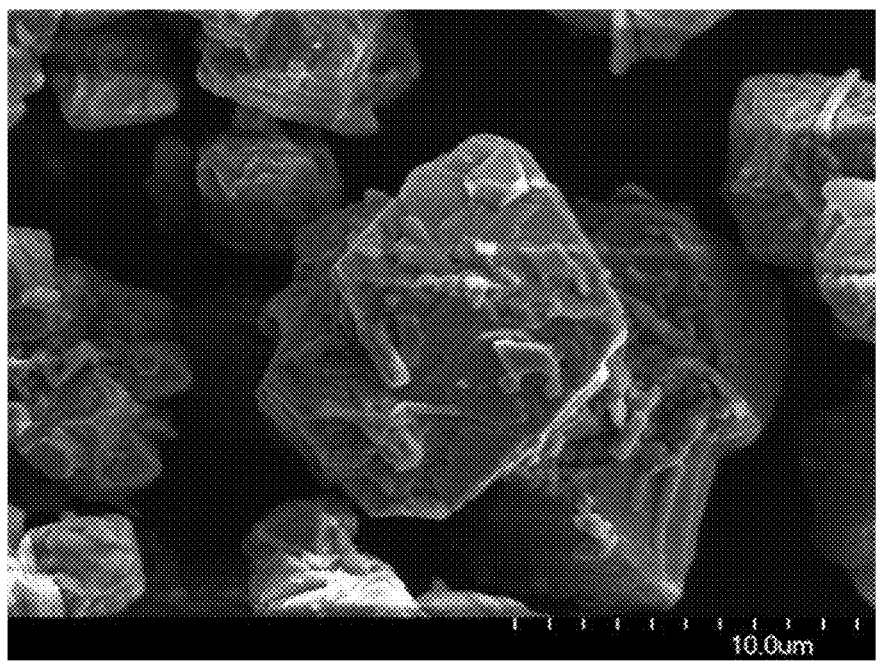
FIG. 7C is a scanning electron micrograph of particles of the lithiated mixed-metal oxide of FIG. 7A at 5000× magnification.

FIGS. 7B & 7C present scanning electron micrographs of particles of the lithiated mixed-metal oxide of FIG. 7A, each at progressively higher magnification (i.e., 2000×, and 5000× magnification, respectively). The micrographs show particles that retain a dense morphology of the mixed-metal oxide (i.e., octahedral crystallites of $Mn_{0.04}Co_{0.96}O_3$). The particles are octahedral-shaped with virtually no voids or pores. No secondary particles are present. Moreover, the particles display a consistent, uniform morphology. A mean particle size, i.e., a D50 particle size, was measured to be 16.2 μm close to that of the mixed-metal oxide of Example 1. D10 and D90 particle sizes were determined to be, respectively, 8.6 μm and 46.0 μm. A tap density of the lithiated mixed-metal oxide was measured at 2.46 $g/cm^3$.

Figure 7D:
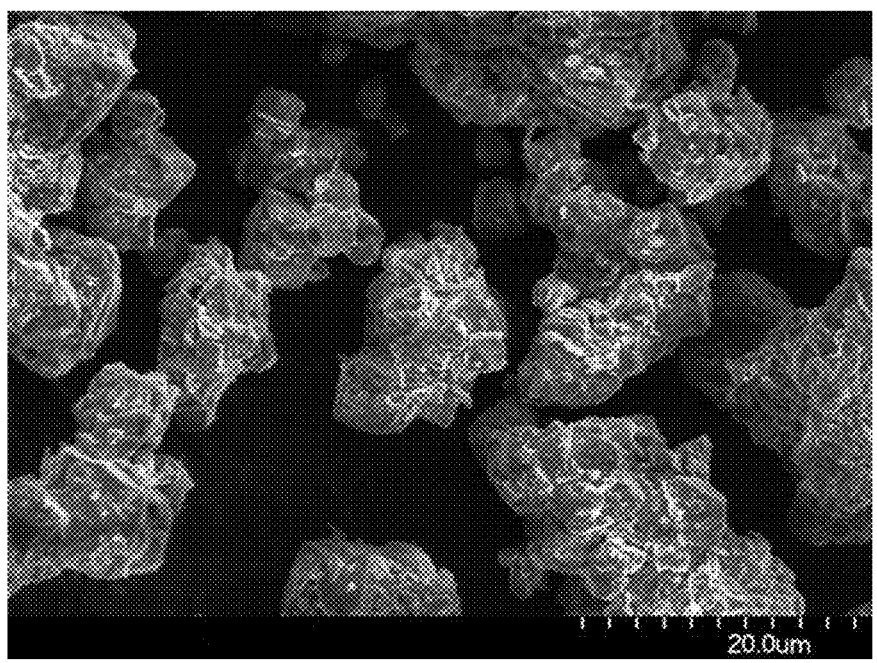
FIG. 7D is a scanning electron micrograph of particles of the lithiated mixed-metal oxide of FIG. 7A at 2000× magnification, taken after pellet pressing at 200 MPa.
Figure 7E:
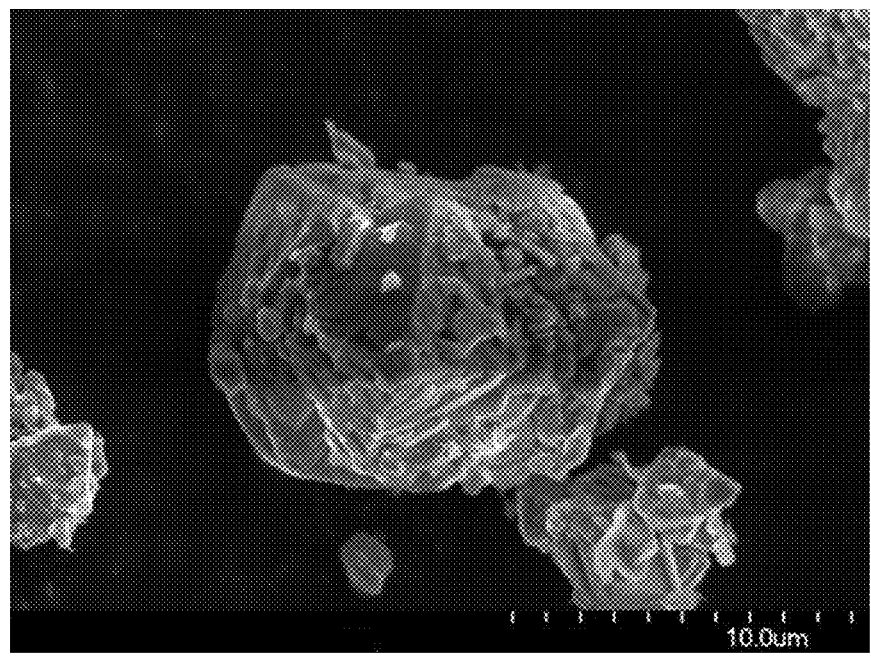
FIG. 7E is a scanning electron micrograph of particles of the lithiated mixed-metal oxide of FIG. 7A at 5000× magnification, taken after pellet pressing at 200 MPa.

Powders of the lithiated mixed-metal oxide $Li_{1.04}Mn_{0.04}Co_{0.96}O_2$ were pressed into pellets under 200 MPa of pressure. Such pressures are similar to those used in calendaring processes to form layers of cathode active materials (i.e., for battery cathodes). A pellet density of 3.62 $g/cm^3$ was measured, strongly suggesting no particle fracture and good particulate strength. To confirm an integrity of the particles, scanning electron micrographs were taken after pellet pressing. These scanning electron micrographs are presented in FIGS. 7D & 7E. A comparison of FIGS. 7D & 7E with 7B & 7C indicates that the particles and their morphologies remain virtually unchanged despite processing under 200 MPa of pressure. No fractured particles are seen in FIGS. 7D & 7E.

Figure 7F:
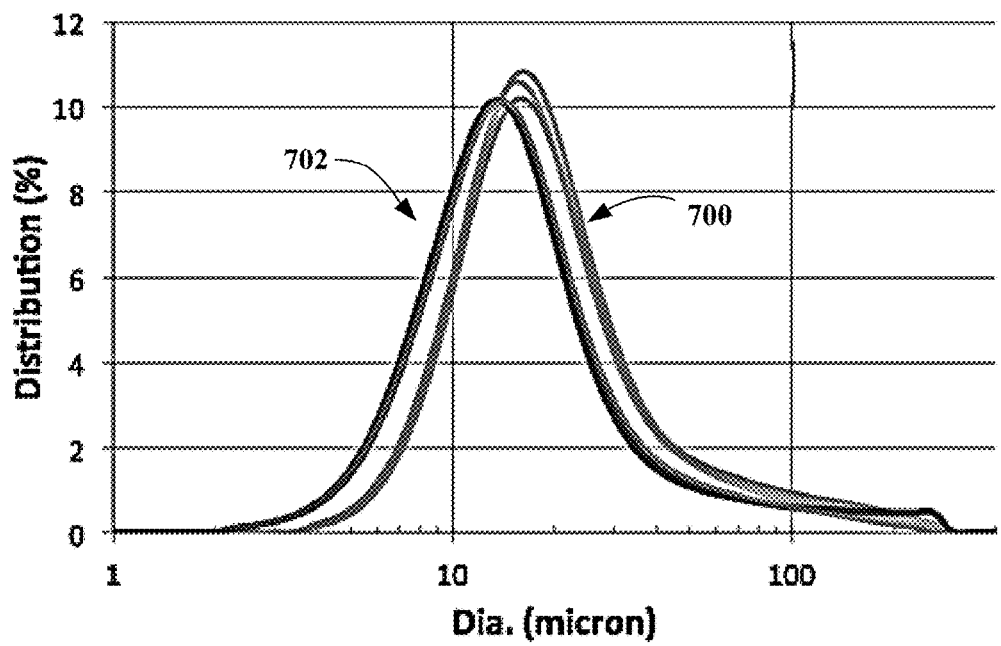
FIG. 7F is a particle size distribution of particles of the lithiated mixed-metal oxide of FIG. 7A, measured before and after pellet pressing.

Particle size analysis was also conducted after pellet pressing. FIG. 7F presents particle size distributions for particles of the lithiated mixed-metal oxides shown in the scanning electron micrographs of FIGS. 7B-7E. A first set of curves 700 corresponds to an initial particle size distribution, i.e., before pressing. A second set of curves 702 corresponds to a post-processing particle size distribution, i.e., after pressings. A shape of the second set of curves 702 remains virtually unchanged relative to the first set of curves. No new peaks emerge. Moreover, the second set of curves 702 is shifted minimally (i.e., about 3 μm) relative to the first set of curves 700. Such measurements indicate that the particles retain their morphologies under high pressure (i.e., >100 MPa) and are strongly-resistant to fracture or crushing.

Example 6—$Li_{1.06}Ni_{1/3}Mn_{1/3}Co_{1/3}O_2$

Figure 8:
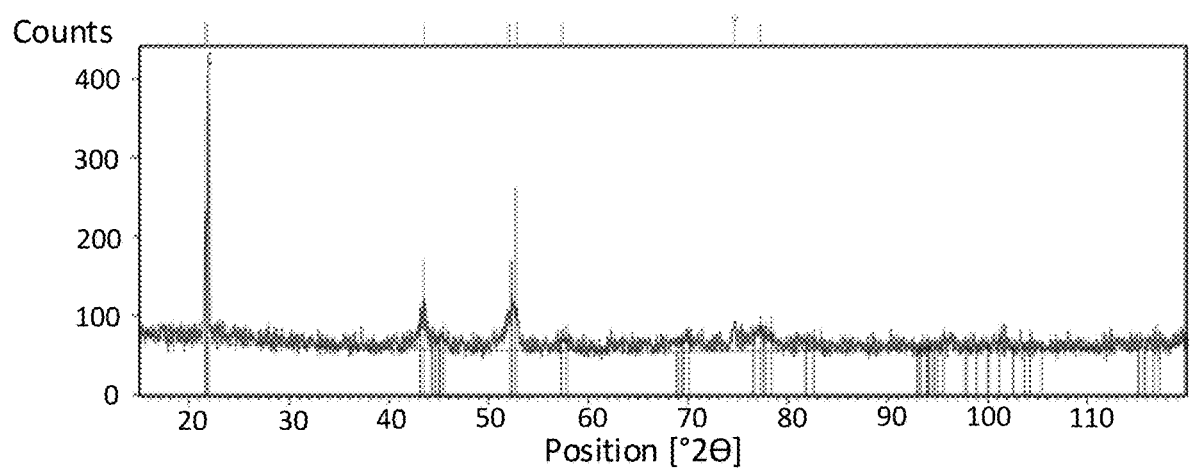
FIG. 8 is a powder X-ray diffraction pattern of the lithiated mixed-metal oxide $Li_{1.06}Ni_{1/3}Mn_{1/3}Co_{1/3}O_2$ according to some illustrative embodiments.

A lithiated mixed-metal oxide $Li_{1.06}Ni_{1/3}Mn_{1/3}Co_{1/3}O_2$ was prepared using the mixed-metal oxide of Example 3 using methods similar to Example 5. Chemical analysis by ICP-OES indicated an [Li]/[Mn,Co] quotient of 1.060. A stoichiometric ratio for Ni:Mn:Co was determined to be 0.337:0.330:0.335. FIG. 8 presents a powder X-ray diffraction pattern of the lithiated mixed-metal oxide. The powder X-ray diffraction pattern reveals a layered, rhombohedral structure (i.e., space group $R\overline{3}m$) with no impurity phases (i.e., single phase). Based on this crystal structure, an atomic oxygen content (i.e., β) was determined to be 2. The phase-pure nature of the X-ray diffraction pattern confirms complete conversion of the mixed-metal oxide $Ni_{1/3}Mn_{1/3}Co_{1/3}O_β$ into its rhombohedral-structured, lithiated derivative $Li_{1.06}Ni_{1/3}Mn_{1/3}Co_{1/3}O_2$. FIG. 1B presents a scanning electron micrograph of particles of the lithiated mixed-metal oxide $Li_{1.06}Ni_{1/3}Mn_{1/3}Co_{1/3}O_2$. (FIG. 1B is also discussed above.) The particles include dense, void- and pore-free primary particles with virtually no secondary particles. Many particles exhibit shapes derived from crystallites of the mixed-metal oxide. As such, octahedral faces and edges are visible in the micrograph of FIG. 1B.

Example 7—$(Co_{0.96}Mg_{0.04})_3O_4$ and $LiCo_{0.96}Mg_{0.04}O_2$

Figure 9A:
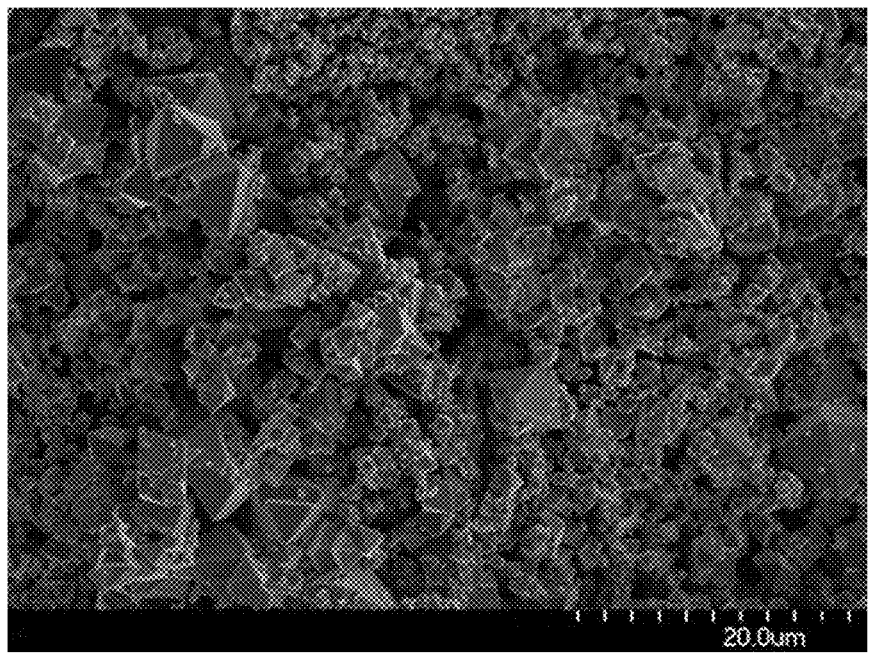
FIG. 9A is a scanning electron micrograph at 2000× magnification of particles of the mixed metal oxide of $(Co_{0.96}Mg_{0.04})_3O_4$, according to some illustrative embodiments.
Figure 9B:
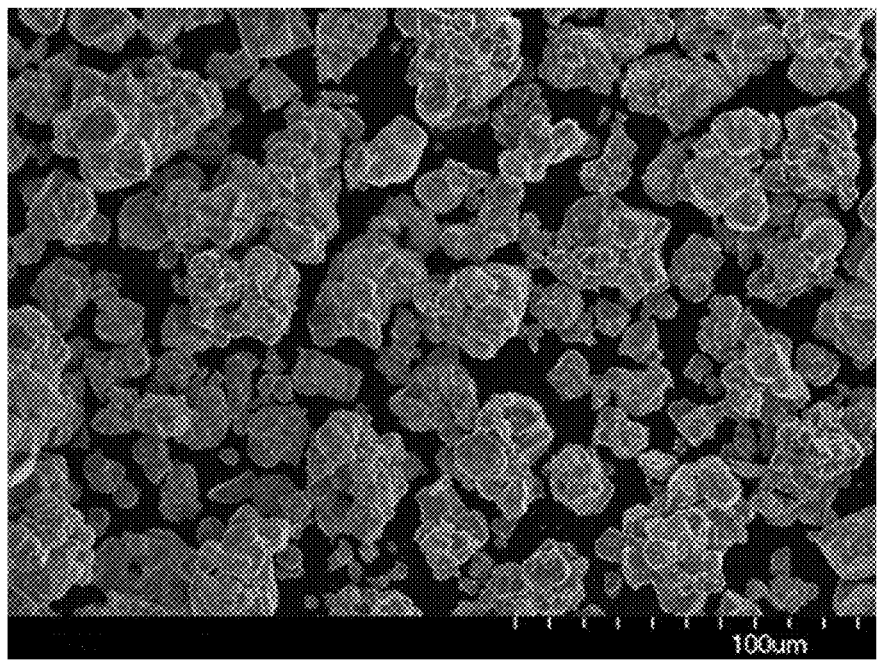
FIG. 9B is a scanning electron micrograph at 500× magnification of particles of the mixed-metal oxide of FIG. 9A, taken after lithiation.

The mixed-metal oxide $Co_{0.96}Mg_{0.04})_3O_4$ and a lithiated mixed-metal oxide $LiCo_{0.96}Mg_{0.04}O_2$ were prepared and analyzed according to procedures analogous to those of, respectively, Example 1 and Example 5. FIGS. 9A & 9B present scanning electron micrographs of the mixed-metal oxide and the lithiated mixed-metal oxide, respectively, at 2000× magnification and 500× magnification. Octahedral crystallites are abundantly present in FIG. 9A, indicating a dense morphology for the mixed-metal oxide. No secondary particles are present. As evidenced by FIG. 9B, this dense morphology is carried over to the lithiated mixed-metal oxide, which consists essentially of void- and pore-free primary particles.

Figure 10A:
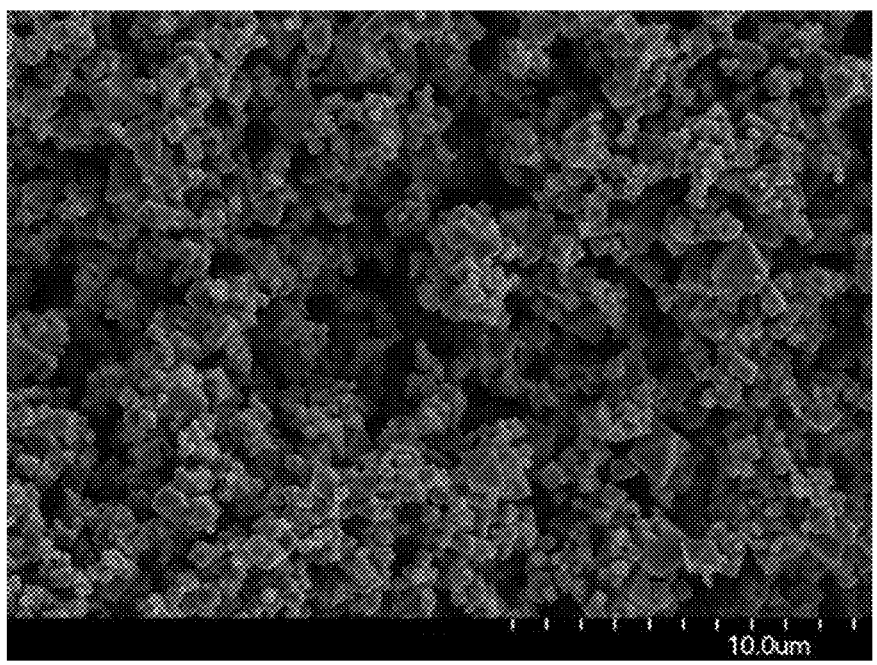
FIG. 10A is a scanning electron micrograph at 5000× magnification of particles of a mixed metal oxide of $(Mn_{0.02}Co_{0.96}Mg_{0.02})_3O_4$, according to some illustrative embodiments.
Figure 10B:
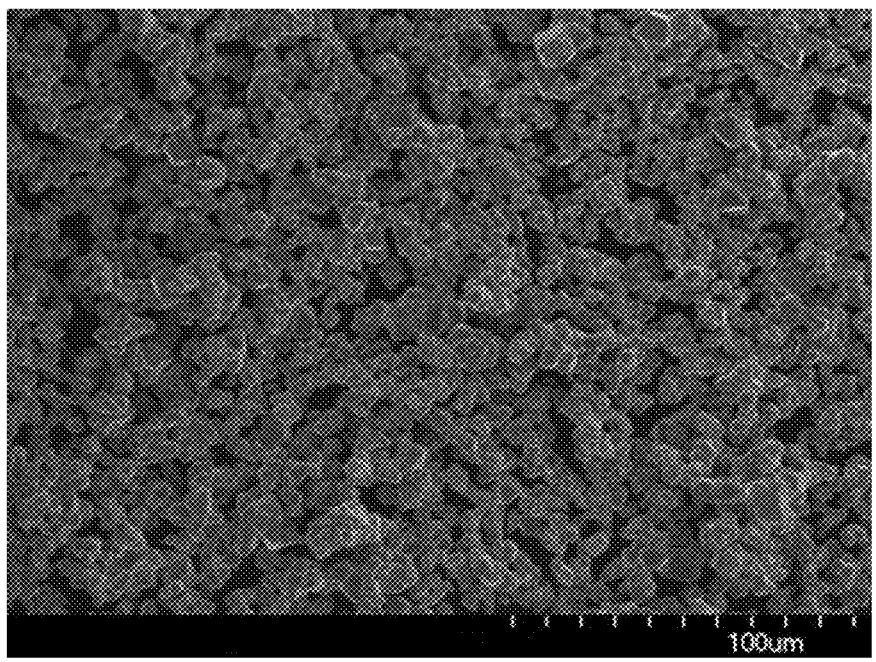
FIG. 10B is a scanning electron micrograph at 500× magnification of particles of the mixed-metal oxide of FIG. 10A, taken after lithiation.

Example 8—$(Mn_{0.02}Co_{0.96}Mg_{0.02})_3O_4$ and $LiMn_{0.02}Co_{0.96}Mg_{0.02}O_2$ The mixed-metal oxide $Mn_{0.02}Co_{0.96}Mg_{0.02})_3O_4$ and the lithiated mixed-metal oxide $LiMn_{0.02}Co_{0.96}Mg_{0.02}O_2$, were prepared and analyzed according to procedures analogous to those of, respectively, Example 1 and Example 5. FIGS. 10A & 10B present scanning electron micrographs of the mixed-metal oxide and the lithiated mixed-metal oxide, respectively, at 5000× magnification and 500× magnification. Octahedral crystallites are abundantly present in FIG. 10A, indicating a dense morphology for the mixed-metal oxide. No secondary particles are present. As evidenced by FIG. 10B, such dense morphology is carried over to the lithiated mixed-metal oxide, which consists essentially of void- and pore-free primary particles.

Example 9—$Li_{1.04}Mn_{0.04}Co_{0.96}O_2$ Incorporated within a Lithium Battery It will be understood that the lithiated mixed-metal oxides presented herein are suitable for use in lithium batteries. For example, and without limitation, the lithiated mixed-metal oxide of Example 5 (i.e., $Li_{1.04}Mn_{0.04}Co_{0.96}O_2$) was further processed into an electrode laminate for a lithium-ion coin cell (i.e., processed as a cathode active material for a lithium battery). The electrode laminate was made by preparing a 90:5:5 weight percent slurry of, respectively, active material (i.e., the lithiated mixed-metal oxide), carbon, and solvent comprising polyvinylidene difluoride (PVDF) binder in n-methyl-pyrrolidinone (NMP). This slurry was cast onto an aluminum current collector sheet using a doctor blade, thereby producing a wet electrode laminate. The wet electrode laminate was dried in air for 4 hours at 75° C. in air, followed by drying under vacuum at 75° C. for 16 hours. The dried electrode laminate was then calendared and circular electrodes punched out (i.e., ⁹⁄₁₆-inch diameter). The circular electrodes were incorporated into size 2032 coin cells (Hohsen, Japan). The coin cells included lithium as a counter electrode (i.e., as an anode); an electrolyte mixture comprising 1.2M LiPF$_6$ salt and a 3:7, by weight, solvent of ethylene carbonate (EC) and ethylmethyl carbonate (EMC), respectively; and a separator formed of Celgard 2325 trilayer propylene.

The coin cells were placed on a Maccor Series 2000 tester and cycled in galvanostatic mode at room temperature within four voltage windows: [1] 4.4V to 2.75V, [2] 4.5 to 2.75V, [3] 4.6V to 2.75V, and [4] 4.7V to 2.75V. A series of electrochemical, formation, rate, and cycling tests were conducted for each voltage window. For cell formation, a constant current of 0.1 C was applied to each coin cell during a charge process. Then, a constant voltage was applied until a charging current was equal to or less than 0.05 C. The coin cells were subsequently discharged at a constant current of 0.2 C until depleted. In this manner, the coin cells were cycled three times through charge and discharge processes. For rate testing, a constant charging rate of 0.7 C was used, followed by a constant voltage until the charging current was equal to or less than 0.05 C. Five different discharge rates, i.e., 0.1 C, 0.2 C, 0.5 C, 1 C, and 2 C, were applied until the coin cells were completely discharged. A total of three cycles were completed for each discharge rate. For cycle life testing, a total of 50 cycles of charging and discharging were conducted using a constant discharge rate of 0.5 C. Conditions for charging were the same as that for rate testing.

Figure 11:
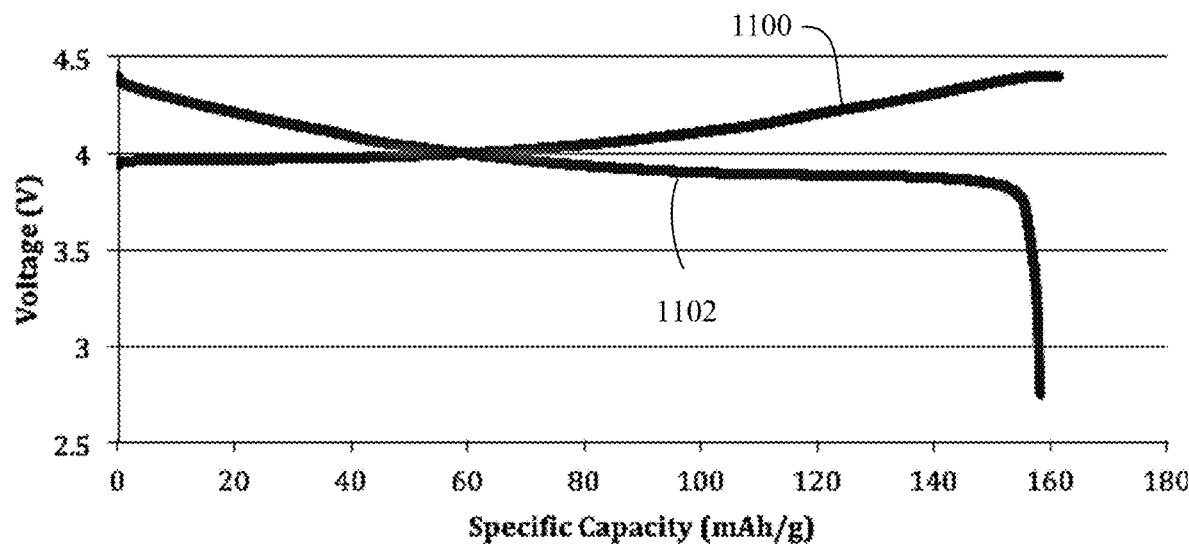
FIG. 11 is a plot of data representing a charge and discharge profile during a first cycle of a coin cell between 2.75 and 4.4 V, according to some illustrative embodiments.
Figure 12:
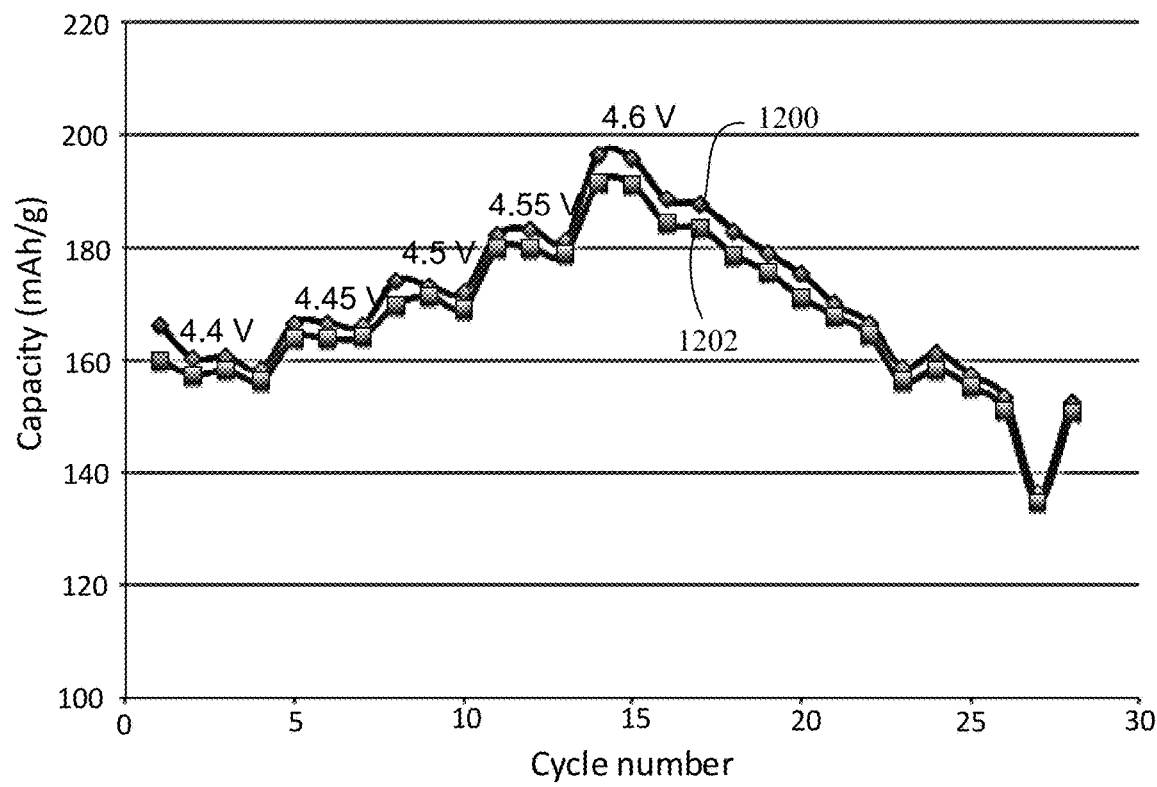
FIG. 12 is a plot of data representing a capacity performance at 4.4 V, 4.45 V, 4.5 V, 4.55V, and 4.6 V of the coin cell of FIG. 11, according to some illustrative embodiments.

FIG. 11 presents a plot of data representing a charge and discharge profile during a first cycle between 2.75 and 4.4 V, according to some illustrative embodiments. Curves representing charging 1100 and discharging 1102 are labeled accordingly. FIG. 12 presents a plot of data representing a capacity performance at 4.4 V, 4.45 V, 4.5 V, 4.55V, and 4.6 V of the coin cell of FIG. 11. Curves representing charging 1200 and discharging 1202 are labeled accordingly.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A compound according to Formula (I):

$$(v)[MnO_2].(1-v)[Co_{1-\sigma}Al_\sigma O_2] \tag{I}$$

wherein
  $0 < \sigma \leq 0.05$, and
  $0.01 \leq v \leq 0.50$.
2. The compound of claim 1, wherein $0 < \sigma \leq 0.03$.
3. The compound of claim 1, wherein $0 < \sigma \leq 0.02$.
4. The compound of claim 1, wherein $0 < \sigma \leq 0.01$.
5. The compound of claim 1, wherein $0.01 \leq v < 0.10$.
6. The compound of claim 1, wherein $0.01 \leq v < 0.05$.
7. The compound of claim 1, wherein $0.01 \leq v < 0.05$.
8. The compound of claim 1, wherein an amount of Al is at least 900 ppm.
9. The compound of claim 1, wherein an amount of Al is less than or equal to 2000 ppm.
10. The compound of claim 1, wherein an amount of Al is less than or equal to 1500 ppm.
11. The compound of claim 1, wherein an amount of Al is less than or equal to 1000 ppm.

* * * * *